United States Patent [19]
Brudny et al.

[11] Patent Number: 5,810,747
[45] Date of Patent: Sep. 22, 1998

[54] REMOTE SITE MEDICAL INTERVENTION SYSTEM

[75] Inventors: Joseph Brudny; Gordon Silverman, both of New York, N.Y.

[73] Assignee: Interactive Remote Site Technology, Inc., New York, N.Y.

[21] Appl. No.: 700,976

[22] Filed: Aug. 21, 1996

[51] Int. Cl.⁶ ........................................... A61B 5/11
[52] U.S. Cl. .................. 600/595; 600/586; 600/587; 600/546; 600/300; 128/924; 434/258; 434/350; 482/9; 482/901; 84/470 R
[58] Field of Search .................. 128/630, 733, 128/774, 782, 903–905, 920, 923, 929; 482/8, 9, 900–902; 434/112, 258, 260, 261, 350, 351; 84/470 R; 600/300, 301, 546, 587, 595, 586

[56] References Cited

U.S. PATENT DOCUMENTS

| | | |
|---|---|---|
| 3,905,355 | 9/1975 | Brudny . |
| 4,375,674 | 3/1983 | Thornton . |
| 4,450,530 | 5/1984 | Llinas et al. . |
| 4,571,682 | 2/1986 | Silverman et al. . |
| 4,712,558 | 12/1987 | Kidd et al. . |
| 4,811,742 | 3/1989 | Hassel et al. . |
| 4,832,033 | 5/1989 | Maher et al. . |
| 4,965,725 | 10/1990 | Rutenberg . |
| 5,020,795 | 6/1991 | Airy et al. ................................. 482/8 |
| 5,078,152 | 1/1992 | Bond et al. ............................. 128/774 |
| 5,082,002 | 1/1992 | Silverman et al. . |
| 5,092,343 | 3/1992 | Spitzer et al. ......................... 128/733 |
| 5,156,158 | 10/1992 | Shirasaki . |
| 5,243,998 | 9/1993 | Silverman et al. . |
| 5,277,197 | 1/1994 | Church et al. . |
| 5,331,550 | 7/1994 | Stafford et al. . |
| 5,331,851 | 7/1994 | Paviainen et al. . |
| 5,390,238 | 2/1995 | Kirk et al. . |
| 5,409,011 | 4/1995 | Alexeev et al. . |
| 5,417,211 | 5/1995 | Abraham-Fuchs et al. . |

(List continued on next page.)

OTHER PUBLICATIONS

Marinacci, A.A. M.D., et al., "Electromyogram In Neuromuscular Re-Education," *Bulletin of the Los Angeles Neurological Society*, vol. 25, No. 2, 1960.

Brudny, Joseph, M.D., "A Single System For Displaying EMG Activity Designed For Therapy, Documentation Of Results And Analysis Of Research," *1976 Conference on Systems and Devices for The Disabled*, Jun. 10, 11, & 12, 1976.

Fausett, L., "Fundamentals of Neural Networks," *Prentice Hall*, 1994.

Comer, D.E., "The Internet Book," *Prentice Hall*, 1994.

Von Altrock, C., "Fuzzy Logic & Neurofuzzy Applications Explained," *Prentice Hall*, 1995.

Silverman, G., et al., "Modern Instrumentation: A Computer Approach," *IOP*, 1995.

*Primary Examiner*—Jeffrey R. Jastrzab
*Attorney, Agent, or Firm*—Kenyon & Kenyon

[57] ABSTRACT

An interactive intervention training system used for monitoring a patient suffering from neurological disorders of movement or a subject seeking to improve skill performance and assisting their training. A patient (or trainee) station is used in interactive training. The patient (or trainee) station includes a computer. A supervisor station is used by, for example, a medical or other professional. The patient (or trainee) station and the supervisor station can communicate with each other, for example, over the Internet or over a LAN. The patient (or trainee) station may be located remotely or locally with respect to the supervisor station. Sensors collect physiologic information and physical information from the patient or subject while the patient or subject is undergoing training. This information is provided to the supervisor station. It may be summarized and displayed to the patient/subject and/or the supervisor. The patient/subject and the supervisor can communicate with each other, for example, via video, in real time. An expert system and neural network determine a goal to be achieved during training. There may be more than one patient (or trainee) station, thus allowing the supervisor to supervise a number of patients/subjects concurrently.

78 Claims, 13 Drawing Sheets

U.S. PATENT DOCUMENTS

| | | | |
|---|---|---|---|
| 5,429,140 | 7/1995 | Burdea et al. | |
| 5,441,047 | 8/1995 | David et al. | 128/670 |
| 5,442,729 | 8/1995 | Kramer et al. | 128/782 |
| 5,452,205 | 9/1995 | Telepko | |
| 5,515,858 | 5/1996 | Myllymäki | 128/774 X |
| 5,533,519 | 7/1996 | Radke et al. | 128/782 |
| 5,544,649 | 8/1996 | David et al. | 128/630 |
| 5,553,609 | 9/1996 | Chen et al. | 128/630 |
| 5,579,378 | 11/1996 | Arlinghaus, Jr. | 128/904 X |
| 5,594,786 | 1/1997 | Chaco et al. | 128/904 X |

REMOTE SITE MEDICAL INTERVENTION SYSTEM

FIELD OF THE INVENTION

The present invention is directed to a computer-based system to assist health providers provide interactive rehabilitative training to patients, and in particular, to a system that allows a health provider to concurrently assist one or more patients who are located at remote sites.

COPYRIGHT NOTICE

A portion of the disclosure of this patent document contains material which is subject to copyright protection. The copyright owner has no objection to the facsimile reproduction by anyone of the patent document or patent disclosure as it appears in the Patent and Trademark Office patent file or records, but otherwise reserves all copyright rights whatsoever.

BACKGROUND OF THE INVENTION

Using mainly instructional techniques—training or teaching—rehabilitation seeks to maximize the potential for independence of living for those individuals who have suffered insults to (or diseases of) the central or peripheral nervous system, injuries or various other abnormalities. However, lacking objective and quantifiable data that reflect the response of movement effectors (muscles) to training, such an approach alone is often less than effective.

The measurement, recording and study of the intrinsic electrical properties of skeletal muscles, or Electromyography (EMG), has been used for over 100 years as a diagnostic modality in order to determine the nature of muscle dysfunction either as result of injury to the nervous system or abnormality of muscle structure. In 1941 Marinacci described the use of needle electrodes in demonstrating the therapeutic value of EMG data obtained from muscles of patients with stroke and peripheral nerve injuries during the retraining process. A review of this technology can be found in the report "Electromyogram in Neuromotor Reeducation" by Marinacci & Horande, (Bulletin of Los Angeles Neurological Society, 25:57 (1960))

This report was generally overlooked by others because of the difficulty in the use of needles and in quantifying "raw" EMG data. In 1972, recognizing the potential of the evolving computer technology, Brudny proposed to utilize the digital computer for processing, quantifying and displaying EMG data obtained from surface electrodes (SEMG), thus giving rise to electromyography as a viable therapeutic modality. He noted that SEMG data, when processed by a computer could provide exteroceptive cues, both accurate and instantaneous, as substitutes for inadequate proprioceptive signals and designated this technique Sensory Feedback Substitution (or SEMG Biofeedback). This technique uses instrumental measures and display of quantifiable variables of disturbed physiologic activities that are otherwise covert, thereby permitting patients to regulate them by gaining control over their own responses. U.S. Pat. No. 3,905,355 (System for the Measurement, Display and Instrumental Conditioning of Electromyographic Signals to Brudny) provided for the acquisition and display of integrated EMG information as well as concurrent display of a simulated ("representative") EMG signal for purposes of comparison with the real information. Although it made no claims for the retraining process, it refers to the usefulness of the instrument as a source of exteroceptive information for a human being whose proprioceptive mechanisms have been damaged by disease. Such information would support retraining providing a human operator intervened. The instrument system was described at a scientific conference by J. Brudny and can be found in the paper entitled "Single System For Displaying EMG Activity Designed For Therapy, Documentation of Results, and Analysis of Research" by Brudny, Weisinger & Silverman, in Conference Proceedings, Conference On Systems and Devices For the Disabled, Boston, Mass. (1976) (Foulds & Lund, Eds).

Human behavior is generally voluntary and goal directed and controlled or modified by its consequences. Some behaviors are followed by positive events (rewards or reinforcers), while other behaviors result in negative events (punishments). When behaviors are followed by rewards, such activities are more likely to be repeated in the future while those behaviors followed by negative events tend to be become less likely to be repeated. The conditioning process by which behavior is shaped underscored by a system of positive (reward) and negative (punishment) reinforcement is referred to as instrumental or operant conditioning. The term "biofeedback" was coined in 1969 to describe experimental findings of experimental animal laboratory studies using operant conditioning techniques wherein various physiologic functions were reportedly brought under voluntary control. This suggested the possibility of applying such techniques to therapeutic environments which has been implemented by Brudny and others in rehabilitation medicine.

Automata, to support instrumental conditioning, have been described and in some instances enjoy patent protection. Examples of these include:

1. U.S. Pat. No. 4,571,682, System and Method for Skill Enhancement and Behavior Modification to Silverman, et. al. that includes: means to operate on Physiological data to produce information that can be readily interpreted by a human observer; calculation of an error between observed responses and one considered to be ideal; a method of improving physical fitness or well being.
2. U.S. Pat. No. 5,082,002, Automatic Operant Conditioning System Especially for Scoliosis to Silverman, et. al. includes means to measure a variable condition, particularly one which underlies willful behaviors and an apparatus that sets criteria which, if not met, may result in negative reinforcement, or if met results in reward. The criteria is automatically adjusted upwards or downwards, in accordance with the subject's history of reaching or not reaching the criteria.

These automata differ in regard to the way in which criteria are automatically adjusted. In neither instance do they alter criteria in a way that imitates a human intelligence, but rely on alterations that follow from meeting a criteria in an all-or-none manner. A human observer would alter the criteria using subjective considerations.

In summary, two historical trends in rehabilitation instrumentation can be distinguished:

1. Development of instruments that acquire physiological data with possible interpretive alteration and display that produces enhanced comprehension regarding underlying physiologic mechanisms that support movement activities.
2. Instruments that support methodologies that implement instrumental conditioning.

A number of existing systems exist to assist health professionals in the treatment, retraining and rehabilitation of individuals suffering from movement dysfunctions as a result of neurological accident or disability. They are primarily devoted to the acquisition of physiological data but may include such features as rectification and integration of EMG signals which results in measures of effort—a concept introduced by Brudny. However, they also suffer from one or more limitations that seriously restrict their ability to restore function in individuals suffering from neurological disorders of movement.

1. They require the presence of a highly alert, exceptionally well trained and qualified therapist virtually all the time. This places an intense burden on the professional and often reduces effectiveness of the therapy.
2. The therapist interacting with one patient at a time makes rehabilitation and retraining programs limited and protracted.
3. The therapist must remain in the immediate vicinity of the patient with loss of flexibility and freedom to carry out other assignments.
4. Using such machines usually limits patient training to increases or decreases of muscle contractions (and often in only a few muscles) instead of those behavior patterns involved in daily living activities such as learning to pick up, and drink a glass of water.

Furthermore, where existing (computer-based) equipment is used to automate rehabilitation and/or retraining of individuals with movement abnormalities the underlying algorithms depend on a fixed rule or calculation with regard to the goals to be achieved by the patient or user. Thus, if the individual exceeds a goal during a training epoch, a new, more difficult target would be established during the next trial. Rather than using an absolute measure, a human trainer, acting without the benefit of a machine, normally scores the patient results in a subjective manner and adjusts the goal in a graded manner. Therefore, existing machines operate in a manner that do not parallel the decision making logic of a human expert in similar circumstances.

SUMMARY OF THE INVENTION

The present invention comprises a system including hardware and software (program) elements which improves the way in which rehabilitation is administered to individuals suffering from neurological disorders of movement or in which training is provided to individuals seeking to improve physical skill performance. The system can be employed to monitor progress and/or control the rehabilitative protocols of one or more individuals in a concurrent manner wherein each person may be undergoing retraining and/or rehabilitation specific to his or her dysfunction or deficit.

The present invention is a computer-based system that assists health providers, such as physicians and other qualified professionals, to provide training to patients and to individuals seeking improved skill performance who may be located locally or at a remote location with respect to the provider. In the representative embodiment, the present invention can support medical intervention for one or more patients in a concurrent manner, even where each of the patients is following a different rehabilitative protocol. Moreover, the present invention includes software modules that provide assistance and guidance to the patient during the rehabilitative training thereby enhancing the ability of the provider to attend to several patients at the same time.

In the representative embodiment, the present invention links a single healthcare professional to many patients, for example, via the Internet. The present invention includes an interactive multimedia format that allows high quality health care to be provided to patients in remote locations, both in the U.S. and throughout the world.

The richness of the software utilized by the present invention provides considerable economy of scale because one expert can readily supervise four or more individuals undergoing training. In the representative embodiment, up to eight patients can be supervised by a single healthcare provider when monitoring is on an event basis.

It will be appreciated that the present invention can also be used for skill training in sports, music and in industry. For the purposes of description, the present invention is described with respect to rehabilitative training. When used herein, the term "patient" should be understood to include any person or subject seeking skill improvement in physical activities and should not be limited to a person simply undergoing medical rehabilitation.

The system of the present invention can be used for a variety of applications involving central nervous system (CNS) and peripheral nervous system insults, diseases, injuries or dysfunctions in humans as well as in skill training in the normal population. CNS insults may include: stroke, cerebral palsy, trauma, incomplete spinal cord injury, Multiple Sclerosis. Injuries or insults to the peripheral nervous system include facial paralysis, brachial plexus injury or injury to the lumbar plexus. (For purposes of description, the present invention will be described primarily with respect to its use in stroke but the principles can be applied to any or all of the conditions previously cited as well as others.)

In the representative embodiment, the system comprises, in part, a network of remotely or locally situated enhanced personal computer (PC) stations which are linked together via a communication system and capable of relaying electronic data that represents physiologic, behavioral, audio and video information. These enhanced resources are referred to as patient stations or trainee stations. One such network of this type is commonly referred to as the Internet and information regarding such networks can be found in the book "The Internet Book" by D. E. Comer, Prentice Hall, 1995. Other computer and communications networks that may be utilized by the present invention include local area networks, wide area networks, public telephone networks, cable networks and the like. A human health care provider (referred to as the supervisor) located at one such station, designated the supervisor station, can guide, direct, and oversee the progress of individuals at each of the remotely located patient stations where the disabled individuals might be located.

In the representative embodiment, each patient station includes a PC enhanced by components for: detecting physiologic signals (e.g., electrodes); measuring and reporting accurate, and objective movement responses (e.g., goniometers); pressure measuring transducers; mechanical stimulation (e.g., vibrators); video and audio communication. Additionally, each PC is augmented with electronic signal amplifiers and conditioners, analog-to-digital (A/D) as well as digital-to-analog (D/A) converters for changing continuous information into discrete, digital form (and from digital to analog form). The PC includes hardware and software support for communication with the other stations in the system, particularly the supervisor station.

The supervisor station is augmented with communication, video and audio components but need not include the A/D, D/A, amplification, conditioning, or transduction elements included in patient stations.

The software organization and operation of the system is under complete control of the supervisor using software modules stored within the supervisor station. All necessary software modules are transferred from the supervisor station to the patient station as required by patient needs. (The process of transferring such software is referred to as 'down-line loading.')

Each patient station includes software means to initiate communication with the supervisor station thereby establishing a link for rehabilitation purposes. (The process of establishing this link is referred to as 'login.') While the login software normally resides within the patient station, it may be down-line loaded from the supervisor station at any time should the version residing within the patient station become corrupted.

During the login operation, patient data and/or history may be recalled from the supervisor station database which forms a part of the system. In cases where the patient is new, the system may initiate determination of historical or other data.

Physiologic and other movement response data from the patient, is obtained from various transduction elements at multiple anatomical sites, converted into PC compatible (digital) form, and is further transformed (synthesized) or converted into data that represents a determination of the patient's muscular, or movement, responses. This information may then be used to control a meaningful display of the underlying information on the PC's monitor such as movement of a virtual representation of part of a human body (e.g., an arm or a face) or possibly generate a sound (audio) or vibration (mechanical) having equivalent representation of the movement response.

The entire ensemble of program elements permits the system to be configured and to operate in one of three modes for each patient station:

A. Manual mode. In this mode of operation the supervisor issues instructions to the patient via either textual commands (on the PC monitor), voice and/or video images or combinations of these facilities. The particular tasks and movements to be attempted, as well as the response goals to be achieved by the patient are determined and set by the supervisor. The supervisor monitors the responses and/or physiologic or other data and may issue additional instructions during the course of the rehabilitative session.

B. Semiautomatic mode. In this mode, automated shaping of patient responses is added to the facilities and resources provided in the manual mode. The supervisor determines the tasks and responses to be attempted as well as the goals to be achieved (e.g., reduce spasticity in the biceps). The supervisor need not—but may, if desired—continually monitor responses in this mode.

Alternatively, semiautomatic operation is achieved when a software module, either downline loaded from the supervisor station or resident in the patient station, monitors the patient's progress and responses and periodically determines a new subgoal to be achieved without intervention by the supervisor. The algorithm for determining the new subgoal imitates the subjective methods (using heuristic means) that a human supervisor might employ and is known to those skilled in the art as Fuzzy logic.

Fuzzy logic is that branch of technology that solves problems which include lexical uncertainty. Humans use words as subjective categories to classify figures such as "spasticity." Using these subjective categories, observations in the real world are evaluated by the degree to which they satisfy the criteria. While a concept may not be precisely defined, humans use them for complex evaluations and decisions that are based on many different factors. They do so by combining the rules that describe similar situations taking advantage of the flexibility in the definition of the words that constitute the rules. To implement these processes (human logic) in engineering solutions—by machine—requires a mathematical model. Fuzzy logic provides such a mathematical model; it allows representation of human decision and evaluation processes in algorithmic form.

While there are limits to what Fuzzy logic can do, it can derive solutions for a given case from rules that have been defined for similar cases. If you can describe the desired performance of a technical system for certain distinct cases by rules, Fuzzy logic will apply this knowledge to produce a solution. The automated shaping of physiologic response is an example of a problem that lends itself to resolution by Fuzzy logic.

C. Automatic mode. In this mode the entire rehabilitative session is under the control of the software modules. The patient may be asked to attempt a standard test movement (e.g., reach for a glass). Physiological and response movement data received at the patient station are transmitted to the supervisor station where the extent of the abnormality, if any, is measured using software known to those familiar with the art as Neural Networks. The results generated by the Neural Network are used to determine a rehabilitative protocol. This part of the automatic process is accomplished using software known to those familiar with the art as an Expert System. The results generated by the Neural Net initiate various rules or conclusions within the Expert System. This also fixes the type of response to be attempted as well as the goals or parametric values (of physiologic data) to be achieved. The response shaping software described within the semiautomatic mode then guides retraining and rehabilitation. The standard test may be repeated from time to time to develop and measure overall progress.

A neural net is a computer program executed on a processor that learns what responses to make based on a series of examples from which it "extracts" the essential characteristic of each class of input. In the present instance, the computer is presented with a number of examples of responses that are considered to be abnormal. While all examples come from an abnormal population, they differ from each other in various ways. The computer learns to identify them by adjusting the weights that it assigns to the various elements of the information. Having once learned to recognize such abnormalities, it can produce conclusions based on these weights for new examples not previously seen.

The Expert System used in this invention is a computer program executing on a computer that implements abductive reasoning or logic. This seeks to imitate the ways in which human beings draw logical conclusions in practice (even though the conclusions may be flawed because this is not perfect logic). Thus, if one knows that a given predicate p implies the predicate q and that q is true at the time it is sampled, we conclude that p must also be true. The result that p is now true can lead to additional abductive results and ultimately to some terminal result which, in this case, is a recommendation regarding a rehabilitative protocol. (The information that is presented to the Expert System comes from the neural net which has specified that a given response is abnormal—the predicate q in the logic noted above.)

The mode to be used is itself determined by the supervisor and he or she may intervene and/or override the current mode at any point in time. Thus, in the automatic mode the supervisor may reject, override or modify the suggestions and/or recommendations proposed by the system with regard to the therapeutic protocol or movement responses to be attempted.

Moreover, software within the supervisor station permits the supervisor to monitor or view the information from any or all of the patient stations in a concurrent manner wherein the monitor of the supervisor station is divided into separate regions or windows in which the selected information from the patient station may be displayed.

Using this information the supervisor is able to provide medical service to several individuals in a concurrent manner.

Accordingly, the advantages of the present invention include an improved system that:

- Is capable of monitoring, controlling or supervising the retraining or rehabilitation of a number of individuals suffering from neurological disorders of movement either in a concurrent or individual manner wherein each individual may have a different deficit or disorder.
- Is capable of monitoring, controlling or supervising the retraining or rehabilitation of a number of individuals who may be remotely located with respect to the source of the control or supervision and each of whom may require a different rehabilitative protocol.
- Includes an improved method for retraining and rehabilitating individuals utilizing a system of computer programs comprising software modules that provide guidance in shaping human responses in a manner that imitates the procedures employed by therapists or other health professionals.

These features and other advantages of the present invention will be better understood from the following detailed description taken in conjunction with the accompanying drawings.

DETAILED DESCRIPTION

Figure 1:
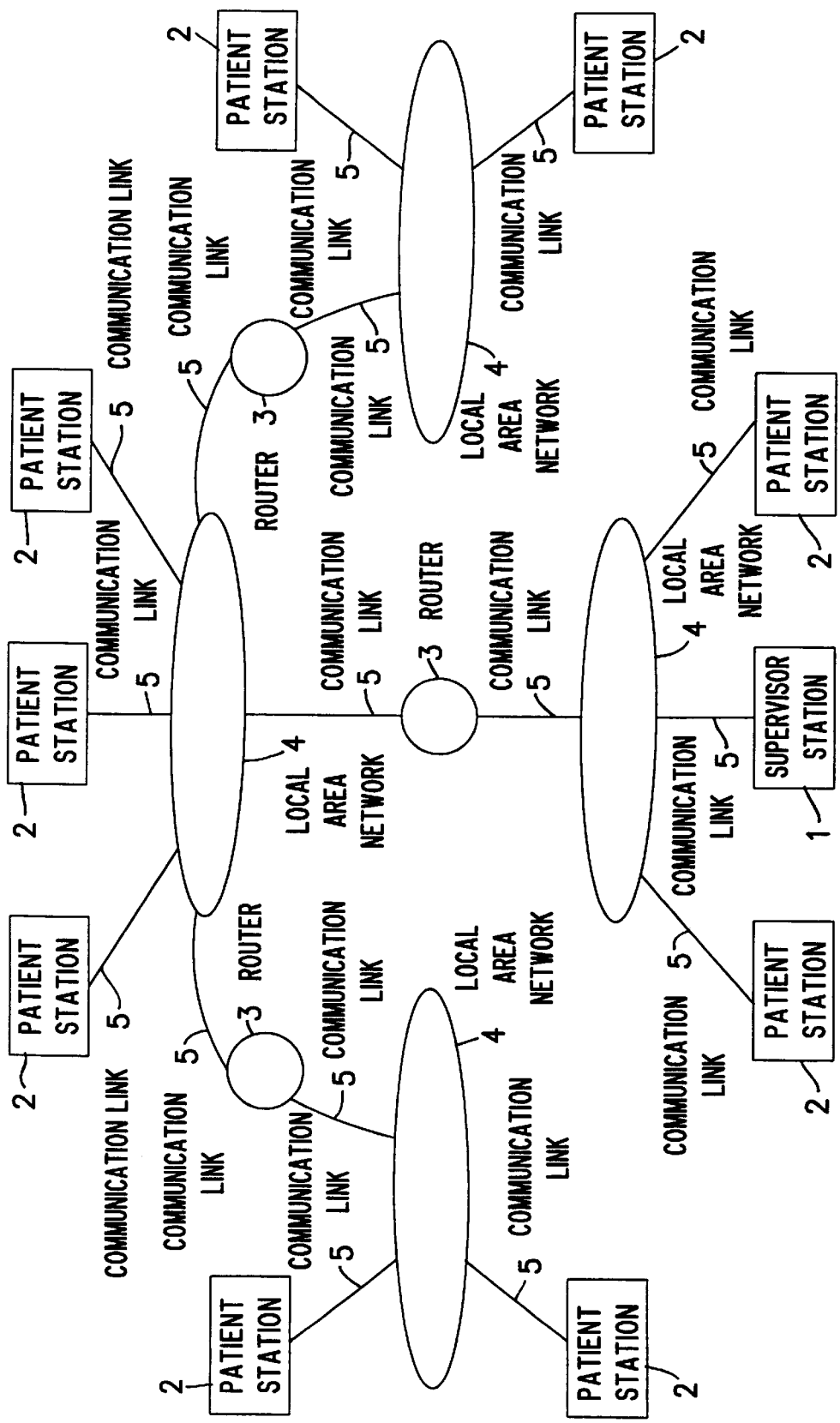
FIG. 1 is a block diagram showing the typical organization or architecture of the remote site medical intervention system of the present invention.
Figure 2:
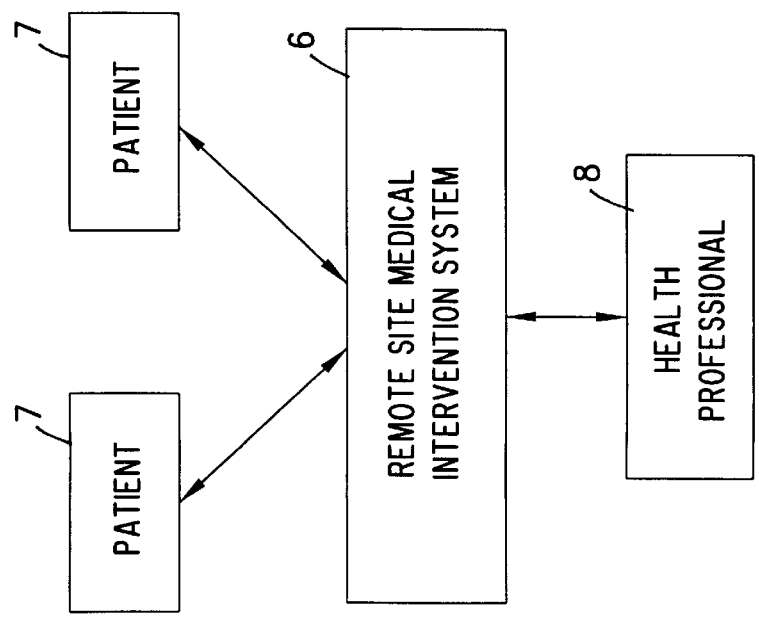
FIG. 2 is a block diagram showing how remotely located patients can receive rehabilitation services from a health professional.

Referring now to the drawings, and initially FIG. 1, there is illustrated in block diagram form a typical organization or architecture of the remote site medical intervention system in accordance with a representative embodiment of the invention. This diagram indicates how a multiplicity of computers are interconnected in order to provide the rehabilitation services to patients who might be located remotely with respect to a health care professional or provider. Taken together, the totality of elements depicted in FIG. 1 comprises network 6 as shown in FIG. 2 which indicates how remotely located patients 7 can receive rehabilitation services from a health professional 8. Interconnections other than the specific configuration shown in FIG. 1 are possible and depend on the distribution and location of patients who receive service as well as the location of the supervisor station 1.

Supervisor station 1 includes all of the programs that serve the locally or remotely located patient stations 2. The supervisor station 1 as well as the multiplicity of patient stations 2 are connected to a local area network 4 via communication link 5. Local area networks 4 connect computers across a short distance (e.g., inside a building) for purposes of communicating or transferring information between the nodes (computers) comprising the network or possibly to nodes located at remote sites relative to the local area networks 4.

Communication among such computers follows a set of rules, or protocols, in order to exchange information in the form of messages. A protocol describes both the format of messages that can be sent as well as the way a computer should respond to each message.

Local area networks 4 consists of a cable to which the computers are attached via communication link 5. Each computer includes an interface board 11 (FIG. 3) to connect the computer to the local area network 4 via communication link 5 which itself is a cable. Alternatively, each, and every, local area network 4 might be replaced by a hub which is an electronic device (as opposed to a cable) that connects several computers together. Communications link 5, consisting of a cable, connects individual computers to the hub. Local area networks 4 may consist of wires that carry the messages (information) in the form of electronic signals. Such wires may be part of a telephone system.

Alternatively, local area networks 4 may consist of optical fibers in which case messages are transferred as variations in the intensity of light carried by such fibers. Interface board 11 (FIG. 3) includes electronic means that convert the information into a form that permits it to travel over longer distances without significant deterioration thereby maintaining its accuracy. Such means might include a modulator and demodulator, or modem. Communication links 5 form part of the system even if local area networks 4 are replaced by hubs which comprise electronic devices or means rather than wires, or optical fibers, to facilitate transmission of the messages.

A special purpose, dedicated (as contrasted with general purpose) computer, attaches to two or more local area networks 4 and forwards messages between local area networks 4 and is denoted as router 3 in FIG. 1. (In alternative configurations, routers may interconnect to other routers instead of local area networks but these architectures ultimately deliver messages between local area networks in a manner similar to the one depicted in FIG. 1.)

Figure 3:
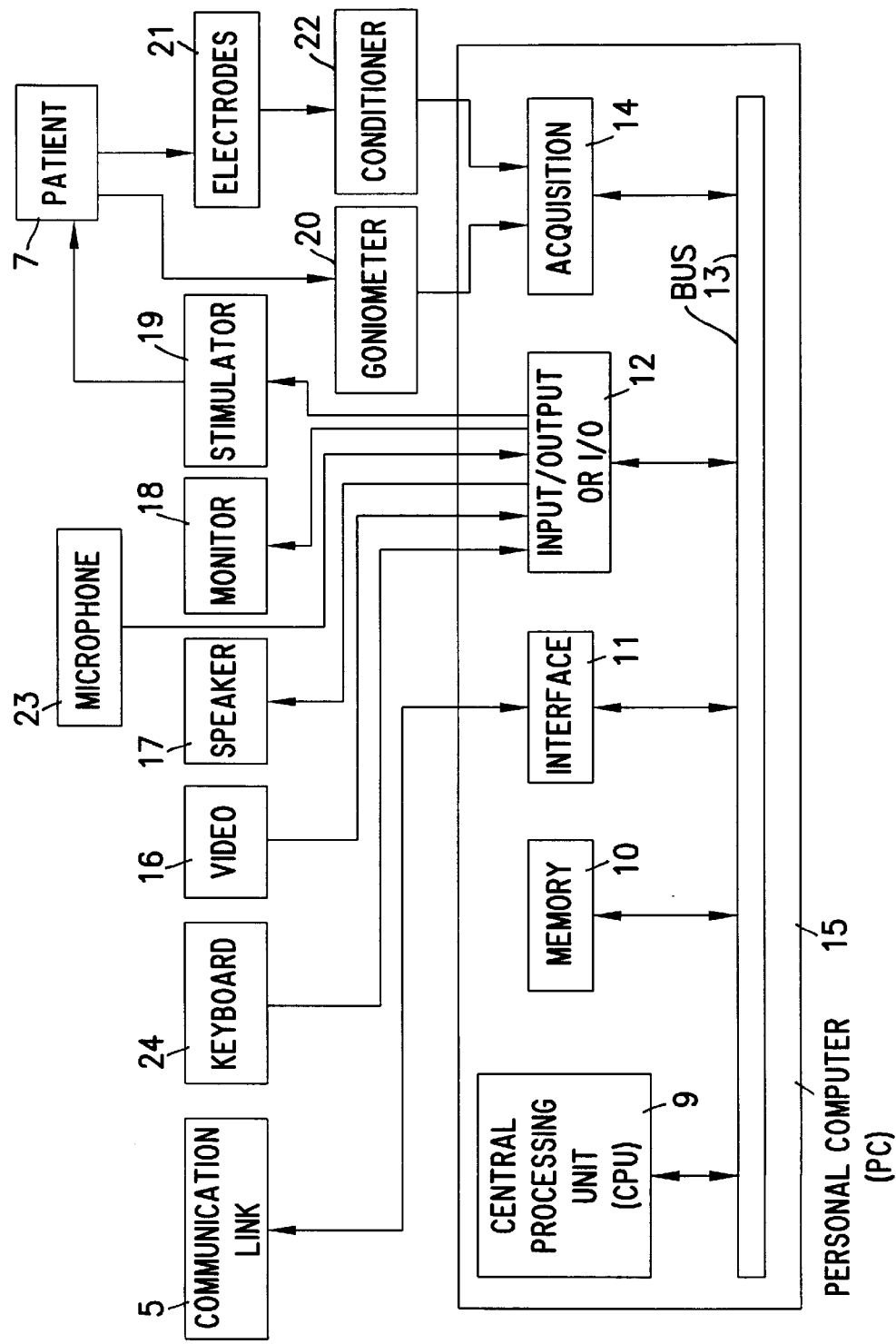
FIG. 3 is a block diagram showing the architecture of a patient station of FIG. 1.

FIG. 3 illustrates the organization of a patient station 2. A personal computer 15 includes the elements needed to: store programs that may be transmitted from supervisor station 1 to patient station 2, store physiologic data, and communicate with various peripheral elements that are needed to provide the rehabilitation services that underlie the remote intervention system. Within personal computer 15, central processing unit 9 executes instructions, performs arithmetic calculations and makes decisions that are required in the processing of information. Computer memory 10 stores programs (instructions), results and intermediate results. Computer interface 11 is needed to communicate with local area network 4 via communication link 5 as previously indicated. Input/output 12 permits personal computer 15 to receive and transmit signals to keyboard 24, microphone 23, video camera 16, speaker 17, monitor 18, and stimulator 19. Data acquisition circuits 14 accept physiologic and positional information from patient 7 after appropriate transformation. The personal computer 15 includes a local communication bus 13 which facilitates the necessary interconnections between central processing unit 9, computer memory 10, computer interface 11, input/output 12 and data acquisition circuits 14.

In normal use, patient 7 generates physiologic signals in muscles which are detected by surface Electromyographic (SEMG) electrodes 21 which produce electrical signals that are representative of the underlying physiologic processes. The signals from SEMG electrodes 21 are amplified and filtered in signal conditioner 22. Electrodes 21 can be replaced or supplemented with pressure sensing devices, and the element electrode 21 when used herein should be so understood.

Amplification increases the magnitude of the signals and filtering limits the frequencies of these signals to the range normally found in humans thereby eliminating any contaminations that may be present such as noise introduced by 60 Hertz fields from any nearby electrical appliances. The amplified and filtered data becomes a signal source for data acquisition circuits 14. Data acquisition circuits 14 translate the information that it receives from a continuous or analog form into a discrete or digital form which can then be acted upon by the other elements of personal computer 15. Computer based data acquisition is discussed in the text "Modern Instrumentation: A Computer Approach" by Silverman & Silver, Institute of Physics Publishing, 1995.

In addition to physiologic information, physical information coming from patient 7, such as joint angle, is converted into a continuous electrical signal by using transducer 20 (goniometer). This information is converted within data acquisition circuits 14 in a manner that is similar to the way that the previously noted physiologic data is converted to digital form.

Keyboard 24 permits the patient (or other human assistant) to enter data into the computer such as might be necessary when taking patient history or to initiate communication with the supervisor station 1 or other purposes. In normal operation the patient 7 may be asked by health professional 8 to answer questions or provide other information. Microphone 23 receives vocal sounds from patient 7 or other human assistant (health extender). Data from microphone 23 is in electrical form and is accepted by input/output 12 which, in part, converts this to a digital form. The converted data can be transmitted to supervisor station 1 via communication link 5, corresponding local area network 4, and appropriate router 3.

In normal operation, health professional 8 might want to have visual contact with patient 7. Video camera 16 obtains images of patient 7 and provides equivalent electrical signals to input/output 12 which, in part, formats these signals, passes them to interface 11 under control of central processing unit 9, which subsequently transmits these images to supervisor station 1 where they can be viewed by health professional 8.

Speaker 17 provides the means by which the voice of health professional 8 can be heard by patient 7. Voice communication is used to send instructions or other information to patient 7 from health professional 8.

Sound from speaker 17 might also correspond to equivalent representations of underlying physiologic processes or physical parameters of patient 7 such as joint angle. Patient 7 can use this information to effect changes in voluntary control of the corresponding physiologic or physical parameter.

Monitor 18 can be used to display textual information or images for patient 7 including those which represent virtual recreations of attempts at movement by patient 7. Such virtual recreations may be stylized or artificial representations so as to effect changes in voluntary control of musculature by patient 7. Information received from the goniometer 20 and electrodes 21 can be synthesized and displayed on monitor 18. In addition, monitor 18 can display an image of health professional 8 for patient 7 in order to demonstrate a movement or for other purposes. The image of health professional 8 might be seen concurrently with sounds from speaker 17 which could carry the voice of health professional 8.

Physiologic or positional information originating from patient 7 and suitably transformed can be converted into mechanical equivalents within mechanical stimulator 19. The result provides a vibratory stimulation of the skin of patient 7 and is another stylized or artificial representation of underlying response attempts.

Figure 4:
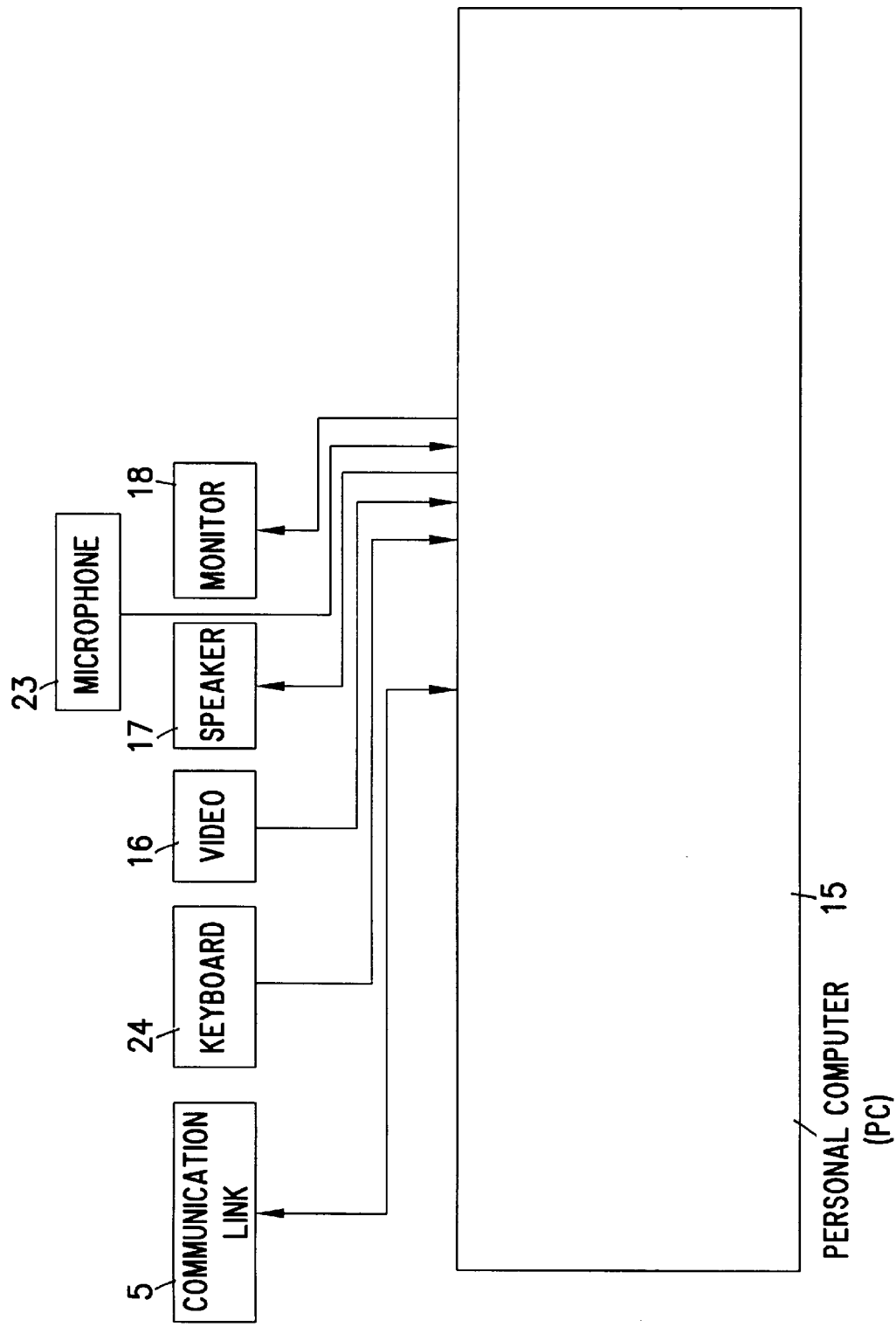
FIG. 4 is a block diagram of the supervisor station of FIG. 1.

FIG. 4 is a block diagram of supervisor station 1. Its components are similar to those of patient station 2. However, it normally does not include those elements which acquire data from patient 7. Supervisor station 1 comprises personal computer 15 and its inherent components with purposes similar to those of the personal computer 15 in patient station 2. While it may include acquisition circuits 14, it should be noted that this is not an essential element of supervisor station 1 as it is not required. It does include: communication link 5, keyboard 24, microphone 23, video camera 16, monitor 18, and speaker 17.

Figure 5A:
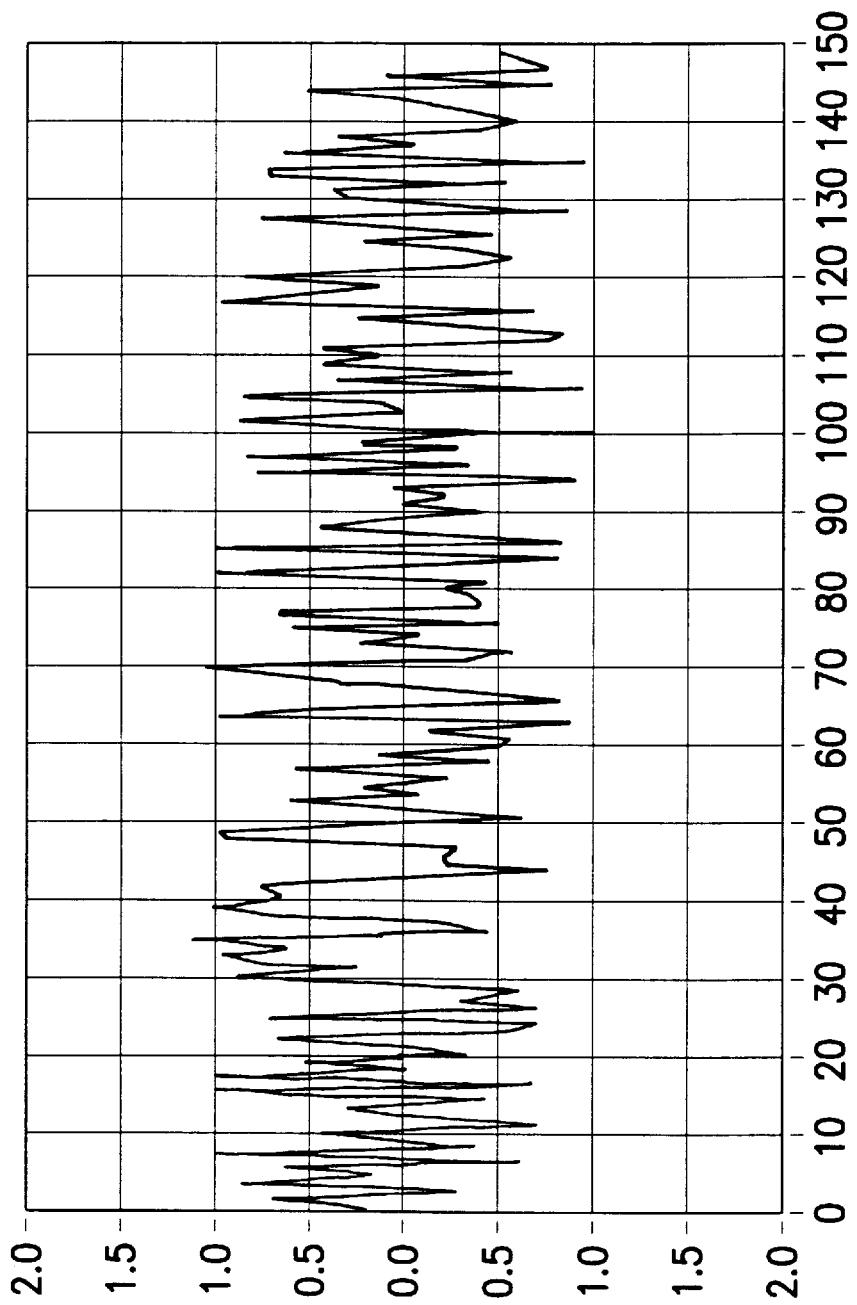
FIG. 5A is a representative signal from SEMG electrodes generated by a normal person from the biceps during a flexion and subsequent release in the sagittal plane.

Electromyographic signals originating in the biceps of a normal person flexing the forearm (in the sagittal plane) and detected by SEMG 21 have an appearance similar to those in FIG. 5A. This is representative of the "raw" EMG. When the raw EMG is subsequently (full wave) rectified, and the rectified signal integrated over short intervals of time (0.1 seconds) in an ongoing or continuous manner the result is similar to the data presented in FIG. 5B. By rectifying and integrating the raw EMG, the result is the work or effort being developed by the pertinent muscle group. A person viewing such information is thereby informed of his or her effort and may thus use this information to alter response. The rectified/integrated signal may be also used to control a virtual representation of the muscle group to convey the same information.

Figure 5B:
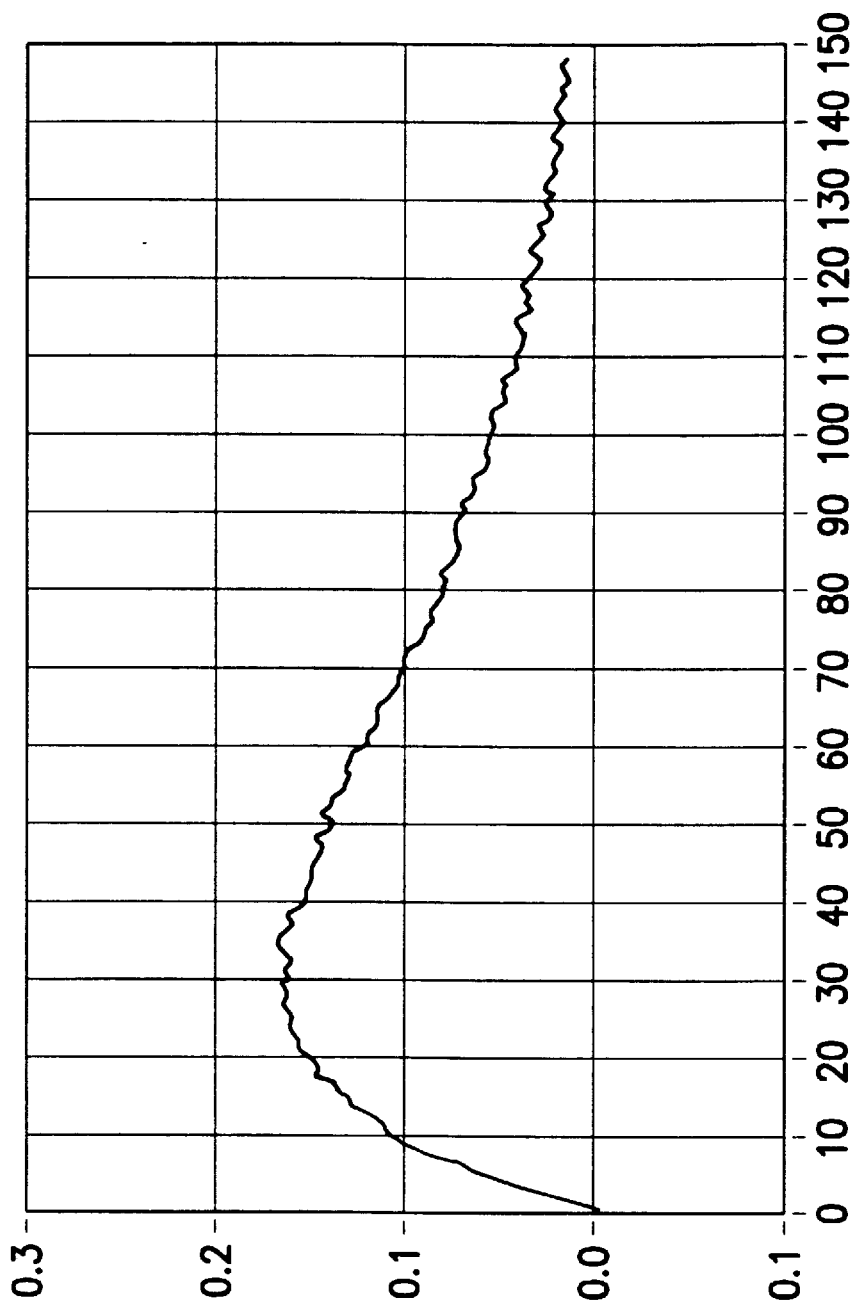
FIG. 5B is the result obtained by full wave rectification of the signal in FIG. 5A and then repeatedly calculating the area under this curve for short intervals of time in an ongoing or continuous manner.

Alternatively, a target or goal similar to the representation presented in FIG. 5B can be displayed for an individual who is then asked to match the effort as a function of time. The person's effort can be displayed in a concurrent manner so as to provide a visual (or auditory) measure of the error or difference between the two signals.

Figure 6:
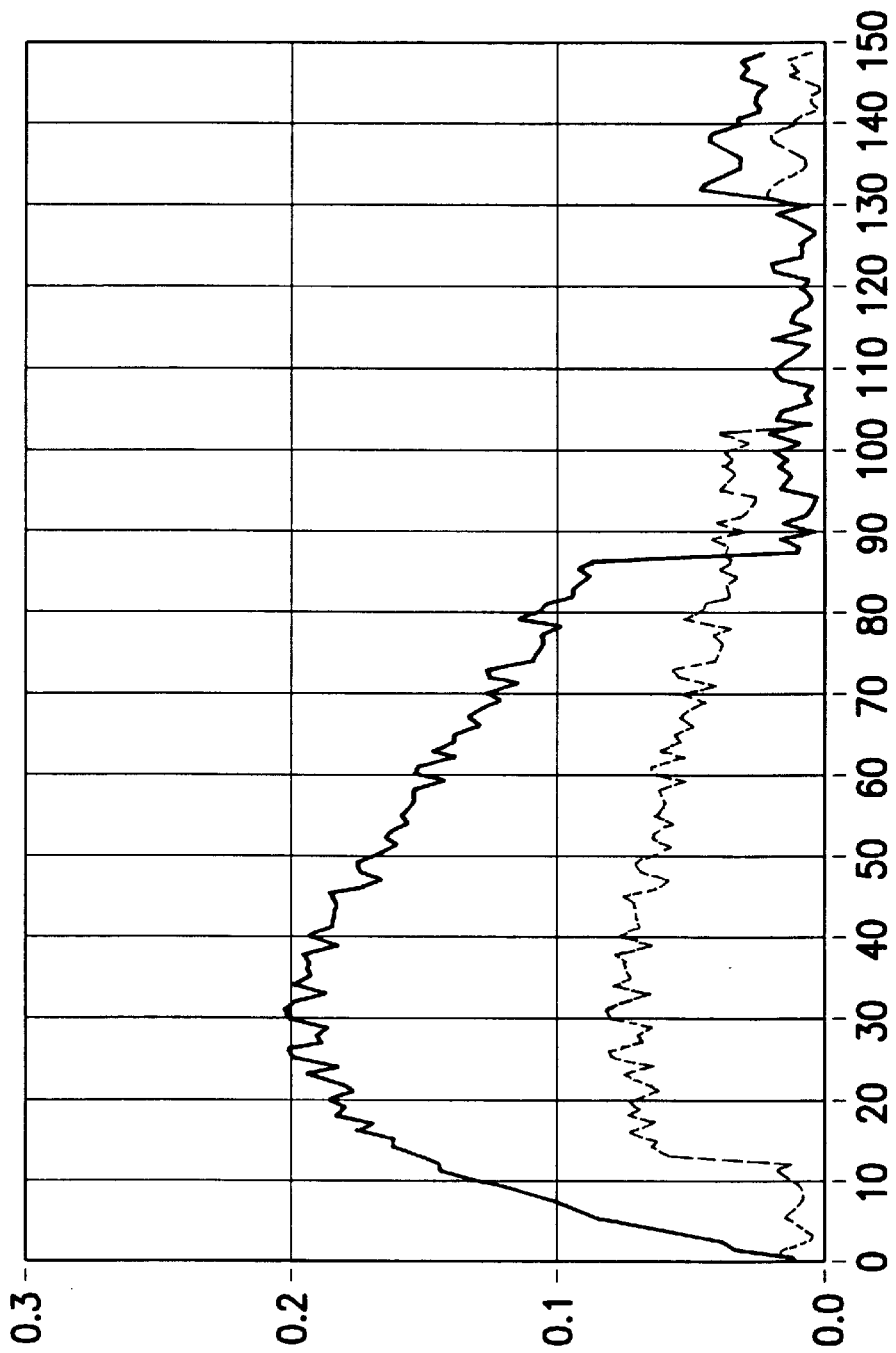
FIG. 6 is a representative plot of the pathological response of a patient who has suffered stroke attempting to perform extension and flexion of the arm. The curves are obtained in the same manner as the one shown in FIG. 5B

A pathological result is generated as shown in FIG. 6 when an individual who has suffered a stroke attempts some motor response such as forearm extension and flexion. In FIG. 6, the solid curve represents the rectified and integrated EMG activity developed from SEMG data (electrodes 21) from the biceps while the dotted curve represents corresponding information obtained from the triceps of the same individual. Both curves show an overlap of effort (activity) which is typical of a spastic response. Spastic response patterns such as those depicted in FIG. 6 can be (automatically) recognized by a computer as will be described below particularly as it relates to the fully automatic mode of operation of the system. In addition, the display shown in FIG. 6 can be presented to the afflicted individual and subsequently used to train that person to eliminate spastic responses.

Alternatively, the information shown in FIG. 6 can be used to animate and control a virtual image (of a limb or other stylized image) from which the individual can similarly learn to modify response resulting in a more normal pattern with an associated improvement in movement.

Figure 7:
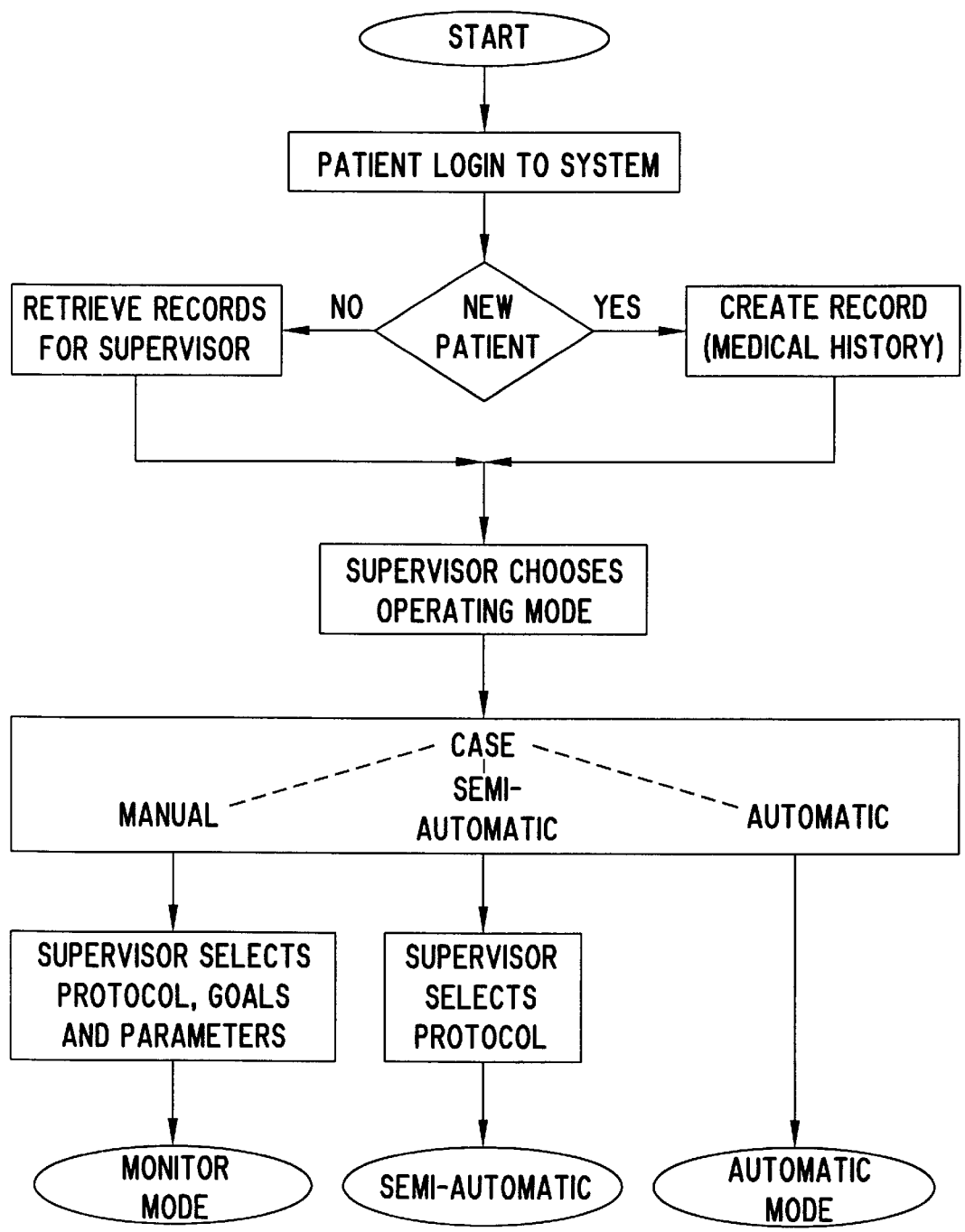
FIG. 7 is a Flow Diagram depicting the initial stages of a rehabilitation session.

FIG. 7 is a Flow Diagram of the start of a rehabilitation session. At the start of a rehabilitation session a software program which resides in memory 10 of each and every patient station 2 can be used to establish initial connectivity between the particular patient station 2 and supervisor station 1. Another individual (e.g., a health extender) can run this program if patient 7 is so physically disabled that he or she cannot complete this task. This procedure is referred to as login. Using the records within a data base of such information stored in memory 10 of personal computer 15 at supervisor station 1, the condition, status and appropriate rehabilitative protocol associated with the individual is retrieved for supervisor 8. If the individual is a new patient the computer will prompt the patient for a medical and personal history and a data base record will be created. Supervisor 8 may then select the manual mode, semiautomatic mode or totally automatic mode. Once this happens, supervisor station 1 will initiate a corresponding software task—monitor mode for manual operation, semi-automatic mode for the semi-automatic choice and automatic mode for the automatic selection. Each patient who is logged into the system from a remote patient station 2 will be controlled by one of the tasks, previously noted, in a concurrent or parallel manner.

Figure 8:
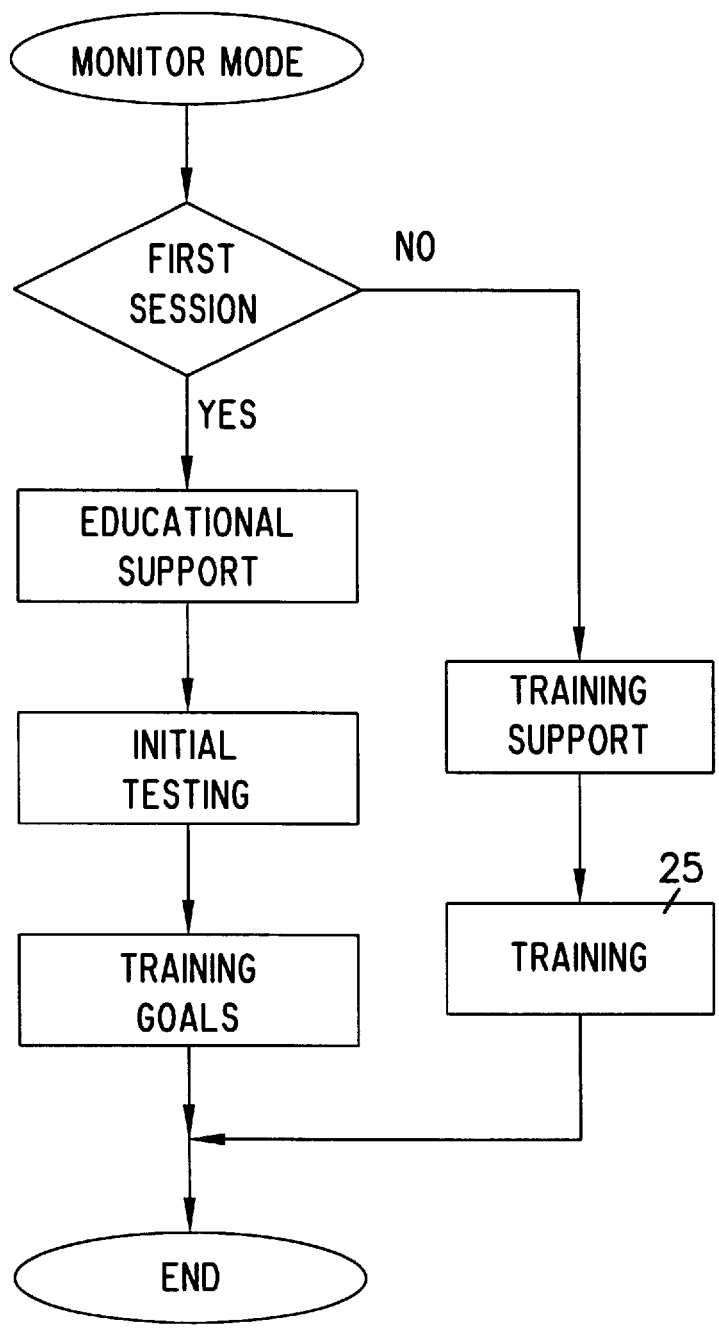
FIG. 8 is a Flow Diagram depicting the processes carried out when a patient is guided by supervisor 8 in manual mode.
Figure 9A:
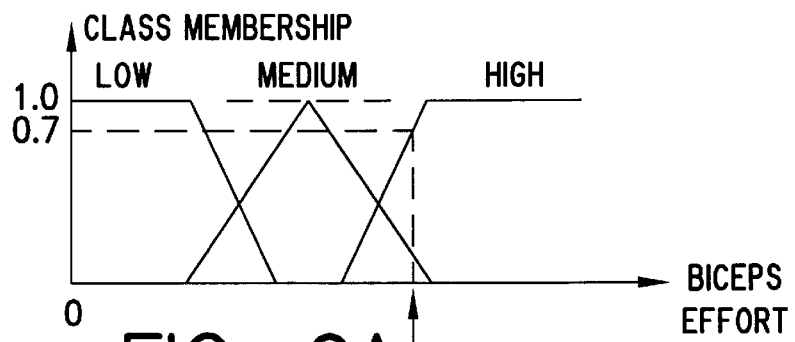
FIG. 9 depicts the Fuzzy logic membership classes for determining response goals during spastic reduction training of a patient suffering from stroke.
Figure 9B:
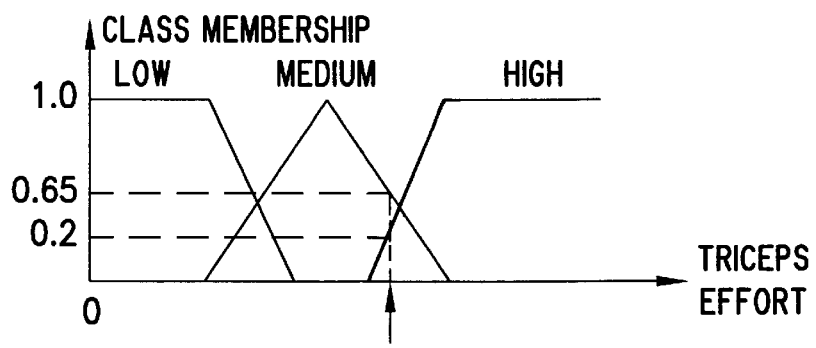
Figure 9C:
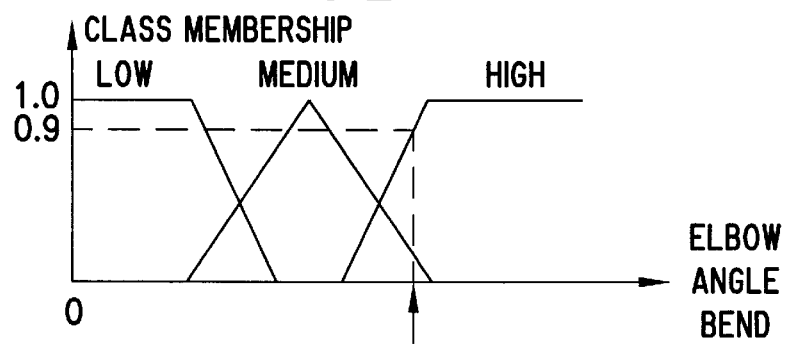
Figure 9D:
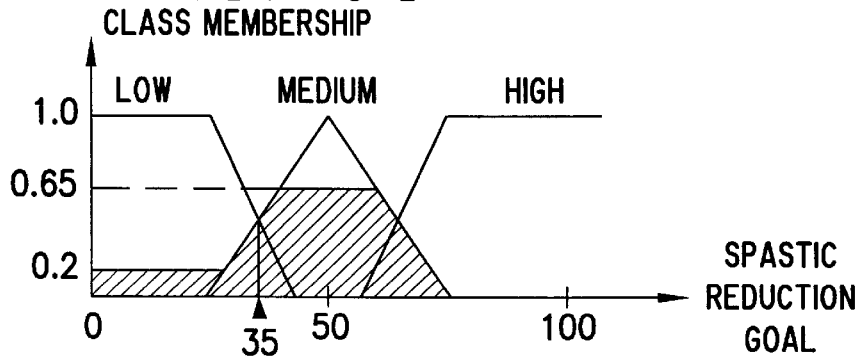

FIG. 8 includes a Flow Diagram that depicts the rehabilitative sessions associated with the manual mode of operation of the system (monitor mode). Not shown if FIG. 8 is the prescreening that an individual completes prior to training. This prescreening is completed in order to determine if an individual qualifies for rehabilitation. To qualify, the individual should meet certain criteria, well known to those skilled in the practice of rehabilitation medicine. For example, the individual should be able to comprehend and retain information and demonstrate some degree of voluntary movement among others. The examining Physician will serve as a "gate keeper" in this respect.

For the first session a patient will receive educational support. This will include a short (3 to 5 minute) presentation (using personal computer 15 on patient station 2) explaining the neurophysiology of voluntary movement in healthy individuals, brain-muscle interaction (feedforward and feedback loops), limb anatomy (segments, spatial displacement at major joints, primary movers), and kinesiology of the upper limb (agonist-antagonist interaction and coordinated and synchronized muscle activity for achieving well defined goals). Protocol defined tasks will then be illustrated and explained (e.g., the sequence of planning and executing a simple task such as reaching out for an object placed on a table top, acquiring it, moving it, and releasing it at a different location.

During the initial testing procedure, the individual may be seated behind a table with a suitable array of electrodes 21 arranged to record and display the muscle's responses (activity) as described above, and range of motion data obtained with an appropriate system of goniometers 20 (and possibly force transducers). A health extender may help to place the transduction elements when the patient can not do so on his or her own. For stroke patients, the affected upper limb is supported by the table top and several protocol defined motions are requested by the examiner to be carried out. The responses being monitored are recorded and displayed visually against a background outline of normal responses for the same motions. The comparison of these two forms a basis for defining the deficit and aiding in formation of training goals as well as ascertaining progress.

Once this is completed, a set of reasonable and modest functional goals is established. Generally (for stroke patients) these will require reduction of spasticity (inhibition), with subsequent increase of activity in weak paretic muscles (facilitation) and their coordinated and synchronized contribution to a simple task (e.g., straightening the elbow). The sequence of training is normally segmental, beginning with proximal segments (arm motion), then proceeding to more distal (forearm) and finally to the "terminal device" (wrist and fingers) for acquisition of objects (prehension). Prehension is of great significance for the ability to care for oneself and engage in some form of work. Gains in prehension render the limb capable of assistive, bimanual activity which is important in the activities of daily living. The initial session may then terminate (end).

The patient may then return for training on a regular schedule until no meaningful gains can be documented within a defined period of training. (Training may be extended for as long as one year, especially when the patient is home bound and training is carried out in the semi-automatic or fully automatic mode with periodic professional evaluation of the course and progress of the recovery and with the assistance of a health extender such as a family member or aide.)

Training in the manual mode (monitor mode) is carried out under supervision of supervisor 8 and is represented by training module 25 in FIG. 8. In general, this individual applies the principals characterized as Operant Conditioning. Guided by supervisor 8, the system trains the individual to establish and sustain adaptive patterns of performance. In cases of neurological disorders of movement individuals have "lost" the ability to perform certain motions that were previously part of their well established repertoire of behaviors. Initially, a simple goal is established (e.g., eliminate spasticity during an attempted elbow extension). The goal appears on monitor 18 of patient station 2 as a criterion line below which the patient is to reduce activity such as that shown in FIG. 6. The patient may only be able to meet this goal with minimal efficiency. However, the smallest correct response is encouraged by positive reinforcers such as a tone that is given as a reward for the patient's efforts. Gradually the patient begins to approach an "acceptable" level of performance and an additional aspect of the recalibration is introduced (e.g., a slight bending of the elbow). If the patient experiences a reversal of performance the system restores training of the simpler task. The process of gradually adding additional elements of the motion continues until the patient has restored as much of the normal activity as possible.

Operation of the system in the semi-automatic mode closely follows the Flow Diagram shown in FIG. 8 (monitor mode). A key difference follows from the process carried out during the training phase. In the monitor mode, training is strictly controlled by supervisor 8. (In particular, supervisor 8 determines how to change the goal as training proceeds.) In the semi-automatic mode goal selection, and hence shaping, is determined by an algorithm that employs Fuzzy logic which alters the response goals in a manner similar to the way in which a human observer would make such decisions including the application of heuristic information gained from past experience.

FIG. 9 depicts the class membership curves that are representative of those that are used in the algorithm for changing goals in the semi-automatic mode of operation of the system during patient response shaping (training). These curves are specific to training an individual for reduction of spastic responses similar to those depicted in FIG. 6.

Predicate calculus, which is the mathematical basis of the digital computer as well as many of the applications which the computer supports (executes), is based on unequivocal definition of classes of objects. However, some situations involving decision making do not lend themselves to unequivocal class membership. Consider a simple example in which the set of all patients having "high fever" is defined as all individuals with temperatures exceeding 102°. Such a definition would define a mathematical function that would uniquely indicate (without any uncertainty) whether or not an individual is a member of that group (set). However, a physician may not choose to make such a restrictive definition but may instead include individuals with lower (or higher) temperatures in the class with some qualifications. These qualifications are the "extent" to which the physician believes that they belong to the class. The physician might conclude that an individual with a temperature of 94° F. would definitely not belong to the class while and individual with a temperature of 105° F. would most certainly belong to the class. In between, the physician would assign an additional characteristic to the temperature known as the "degree of membership" which reflects "belief" (uncertainty) that the given temperature belongs to the class. A class membership value of 0 means that the given value (definitely) does not belong to the class while a class value of 1 indicates that the given value (definitely) does belong to the class. (A class value of 0.5 suggests that the value belongs to the class with a certainty of 50%.) Class membership parallels (mimics) a human belief system as it approximates the extent to which an observation belongs to a particular class.

The modeling (and machine implementation) of the linguistic uncertainty described above is known as Fuzzy logic. It also provides the mechanisms for drawing "firm" (or "crisp") resolutions to logical problems in a manner that mimics human thought processes. Consider now how Fuzzy logic is applied to response shaping (training) algorithms of individuals with neuromotor disorders of movement. In particular, consider how it is applied in the present invention to inhibition of spastic biceps muscle activity (during facilitation of paretic triceps) for extension of forearm. (Such response is common in individuals who have suffered stroke.)

FIG. 9 includes class membership curves for three aspects of a forearm extension response, namely the biceps effort, the triceps effort and the extent (angle) of elbow bend. For each of these characteristics, three classes are identified (low, medium and high). Thus, biceps effort (as well as the other characteristics) may belong to low, medium, or high classes. The extent to which biceps effort belongs to each class can be found by noting the class membership value on the ordinate axis. (At a value of biceps effort indicated by the arrow, the extent (class membership value) to which it belongs to the high (effort) class is 0.7. It also belongs to the medium class because it intersects that membership curve. It does not belong to the low membership class.). For some range of biceps effort, a human observer (expert) might classify biceps effort as "low" with a certainty of 100%; the ordinate value of this condition is 1.0. As biceps effort increases, an expert may quantify such response as low but "not entirely so." Thus, the certainty of belonging to the class designated as "low" gradually decreases until it is no longer considered to belong to the class designated as "low;" the certainty is reduced to 0%. However, some values of biceps effort may be considered to belong to both the "low" class (with some certainty) or to the "medium" class (with some different certainty). Interpretation of class membership may also be extended to the class designated as "high" in a similar manner. (The abscissas in the case of biceps effort, triceps effort, and elbow angle bend are considered to have arbitrary units.)

Determination of response goals proceeds according to a system of rules. For example, when the system is operating in the manual mode, supervisor 8 might rely on the following subjective or "practical" (heuristic) rules for adjusting goals during inhibition training of spastic biceps muscle activity:

Rule 1:
    IF (biceps effort is high) AND (triceps effort is high) AND (elbow angle bend is high) THEN (spastic reduction goal is low).

Rule 2:
    IF (biceps effort is high) AND (triceps effort is medium) AND (elbow angle bend is high) THEN (spastic reduction goal is medium).

(The rules are presented as predicates rather than in the vernacular to simplify machine implementation.) These rules can be quantified and the amount of spastic reduction resolved using techniques from Fuzzy logic. (Details regarding the theory and use of Fuzzy logic can be found in "Fuzzy Logic & Neurofuzzy Applications Explained" by Von Altrock, Prentice Hall PTR, 1995.) In this example assume that the averaged results from several response attempts from patient 7 produce the values denoted by arrows on the abscissas of biceps effort, triceps effort, and elbow angle bend in FIG. 9.

Rules 1 and 2 (above) are evaluated in the following way:

1. Evaluate the phrase "biceps effort is high." To do so, examine the HIGH class membership graph for the BICEPS EFFORT characteristic. The value of effort denoted by the arrow intersects the HIGH membership graph at a value of 0.7. This is the certainty associated with the indicated value of BICEPS EFFORT—the arrow.

2. Repeat this evaluation for the phrase "triceps effort is high"—the second graph. The value returned here is 0.2.
3. Repeat this evaluation for the phrase "elbow angle bend is high." The result returned is 0.9.
4. To operate on the three phrases evaluated in steps 1, 2, and 3 as defined by the AND operation, we use the following formula from the mathematics of Fuzzy logic:

$$\mu_{A \wedge B \wedge C} = \min(\mu_A, \mu_B, \mu_C)$$

where $\mu$ signifies the class membership value (certainty) and $\wedge$ designates the AND operation. A, B, and C specify the defining characteristics (e.g., A=biceps effort). The belief in the joint valuation of the three phrases is obtained by finding the minimum of the certainty over the three defining phrases. In the present example that value is 0.2 from the following—class membership values taken from the graphs in FIG. 9:

| characteristic | class membership value |
| --- | --- |
| biceps effort is high | 0.7 |
| triceps effort is high | 0.2 |
| elbow angle bend is high | 0.9 |

The minimum of these three class membership values is 0.2.

5. Repeat this procedure for Rule 2. The phrases to be evaluated and their corresponding class membership values are:

| characteristic | class membership value |
| --- | --- |
| biceps effort is high | 0.7 |
| triceps effort is medium | 0.65 |
| elbow angle bend is high | 0.9 |

In this case the result of the AND operation is 0.65 as that is the minimum of the intersection of the three class membership values.

6. Rule 1 specifies that "spastic reduction goal is low" while Rule 2 specifies that "spastic reduction goal is medium." An overall conclusion as to goal setting requires that these two heuristic results need to be resolved. This is accomplished by weighting the results produced by steps 4 and 5. (Each of these steps propose a value for the amount of "spastic reduction goal.")

Two weighting (resolution) algorithms are possible—each of these mimics human decision and evaluation processes. Both use a two step process:

(a) A "typical" value is computed for each term in the linguistic variable. (This was completed in steps 4 and 5.)
(b) A "best compromise" is determined by "balancing" out the results.

Figure 10:
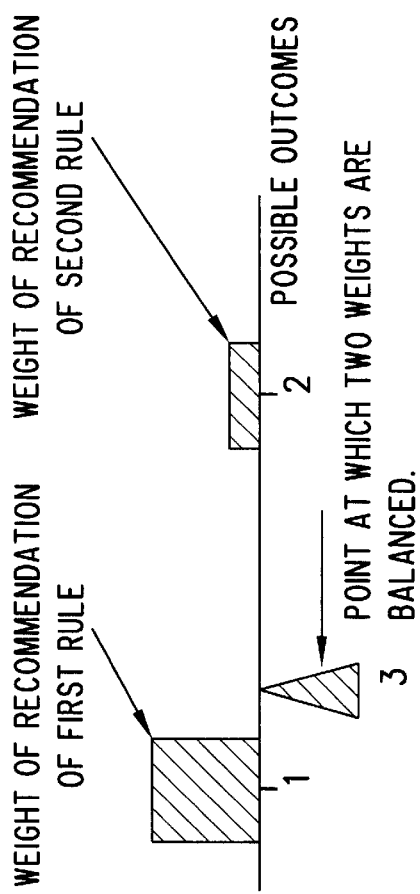
FIG. 10 describes the center of gravity method for resolution of Fuzzy logic processes ("defuzzification").

In this example the "center of gravity" method is employed because it best represents the logic that an expert or therapist would employ if confronted with making a decision based on the observations noted above. The method is illustrated in FIG. 10 (for a generic problem not specifically to the present example). The axis shows an arbitrary range of choices that are possible. Two recommendations are suggested together with their representative weights. The first rule is centered on 1 with a strong recommendation while rule 2 is centered on 2 with a weaker recommendation. The balance shows the point (on the axis) where the two rule recommendations are balanced. This value (3) is the resulting outcome.

FIG. 9 illustrates the resolution of the spastic reduction goal. Calculations from Rule 2 propose any medium spastic reduction goal whose class membership value is below 0.65. Calculations from Rule 1 propose any low spastic reduction goal whose class membership value is below 0.2. (These correspond to the choices shown in FIG. 10.) For the present case—curve 4 of FIG. 9—the two weights are balanced at a spastic reduction goal of 35 as indicated by the arrow. This number provides a training goal that should be set (on a scale of 0 to 100) for the individual whose spastic reduction is being shaped at this particular point in the treatment cycle. The individual seeks to match his or her response to the goal that has now been set. This goal may appear as a target response on monitor 18 or as a virtual image on monitor 18.

The system periodically repeats this calculation for the individual and adjusts the spastic reduction goal according to the results. Once the spastic response has been reduced, facilitation of the paretic triceps can be accomplished. The resulting spaciotemperal control that the individual achieves is thereby restored to more normal boundaries. Initial targets can be derived from records produced by the individual from flexion/extension trials of an unaffected limb.

Figure 11:
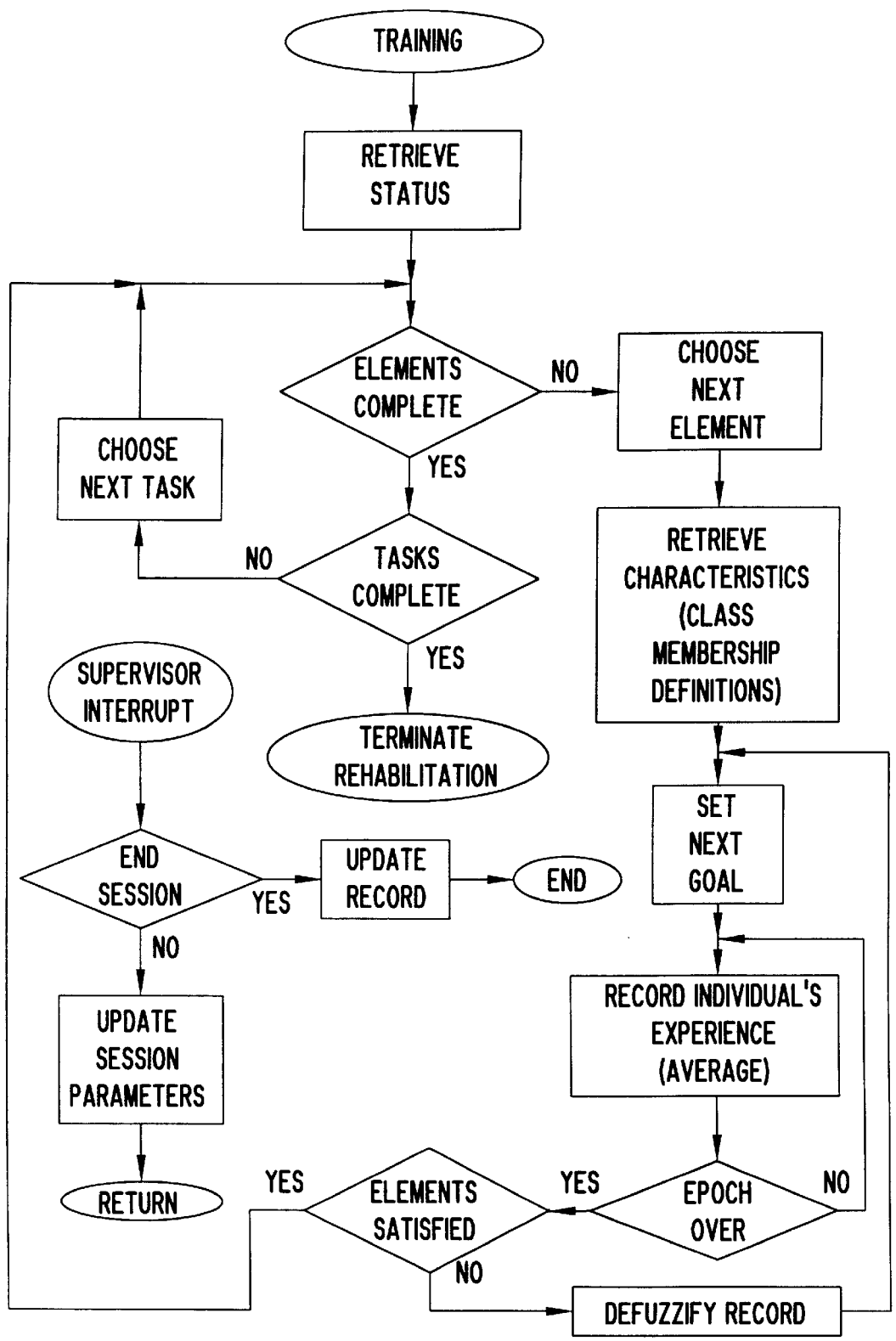
FIG. 11 is a Flow Diagram describing the training procedure module 25 in the semi-automatic mode of operation of the system.

A Flow Diagram for the training module 25 of the semi-automatic mode is shown in FIG. 11. A rehabilitation protocol consists of a series of (training) tasks and these tasks, in turn, may consist of subtasks which are further decomposed into a series of elements. For example, the protocol for individuals who have been afflicted with stroke would consists of maximizing restoration of normal function to affected limbs so that the normal activities of daily living can be restored. Tasks for this protocol (stroke rehabilitation) might include restoration of drinking a glass of water and learning to put on one's clothes among others. Learning to reach for, pick up a glass of water, bring it to the mouth and drink it might include a number of subtasks such as restoring the flexion and extension response in various planes (e.g., sagittal and transverse) of both arm, forearm, wrist and fingers, as well as adductive movements where appropriate. Each task is then segmented into a series of elements such as the sequence of first training inhibition of spastic muscles followed by facilitation of the appropriate agonist or antagonist.

In the semi-automatic mode the individual's status is first accessed by personal computer 15 at subject station 2 from the supervisor 1 data base. The individual's status includes the relevant protocol, the tasks required under this protocol and whether or not the individual has successfully completed each task, and finally the task elements and their status (e.g., completed). Once all elements and all tasks have been completed, the rehabilitation is considered to be terminated (or suspended in some instances).

If some elements remain to be completed, one of these is taken from the list. The class membership definitions for this task are retrieved from the supervisor 1 station data base (e.g., biceps effort, triceps effort, elbow angle bend). The next goal to be achieved is determined—this data can come from the individual's status information. The individual attempts to meet this goal; his or her attempts are recorded and a running measure of the experience (e.g., the average)

is maintained in the personal computer 15 of patient station 2. After a number of trials or a period of time specified by the task, the individual's experience is evaluated in accordance with the rules of Fuzzy logic as previously described. If the element has not be satisfied because the individual has not reached an acceptable goal for this element, a new goal is established through DEFUZZIFICATION as previously noted.

If the element is satisfied at the time that it is evaluated—at the end of the epoch (trial)—the system checks to see if all elements are complete. If all elements are complete, the list of tasks in the protocol is checked.

If this list has been processed, rehabilitation is terminated. The tests are all carried out at the supervisor station 1 and if new tasks are required these are transmitted to patient station 2 over local area network 4, and router 3 (if appropriate).

Physiologic, visual, audio and as well as the experience of patient 7 is transmitted over local area network 4 and router 3 (if appropriate) to supervisor station 1 where it is available for review by supervisor 8 at any time. Supervisor 8 may interrupt operation of any patient station 2 during the semi-automatic operating mode. Supervisor 8 may either decide to terminate the session, issue new instructions and/or update parameters. If the session is ended, the patient's record is updated and the session terminated. Alternatively, the session returns to the point at which it was interrupted if supervisor 8 has not terminated the session but changed the conditions (e.g., parameters).

Figure 12:
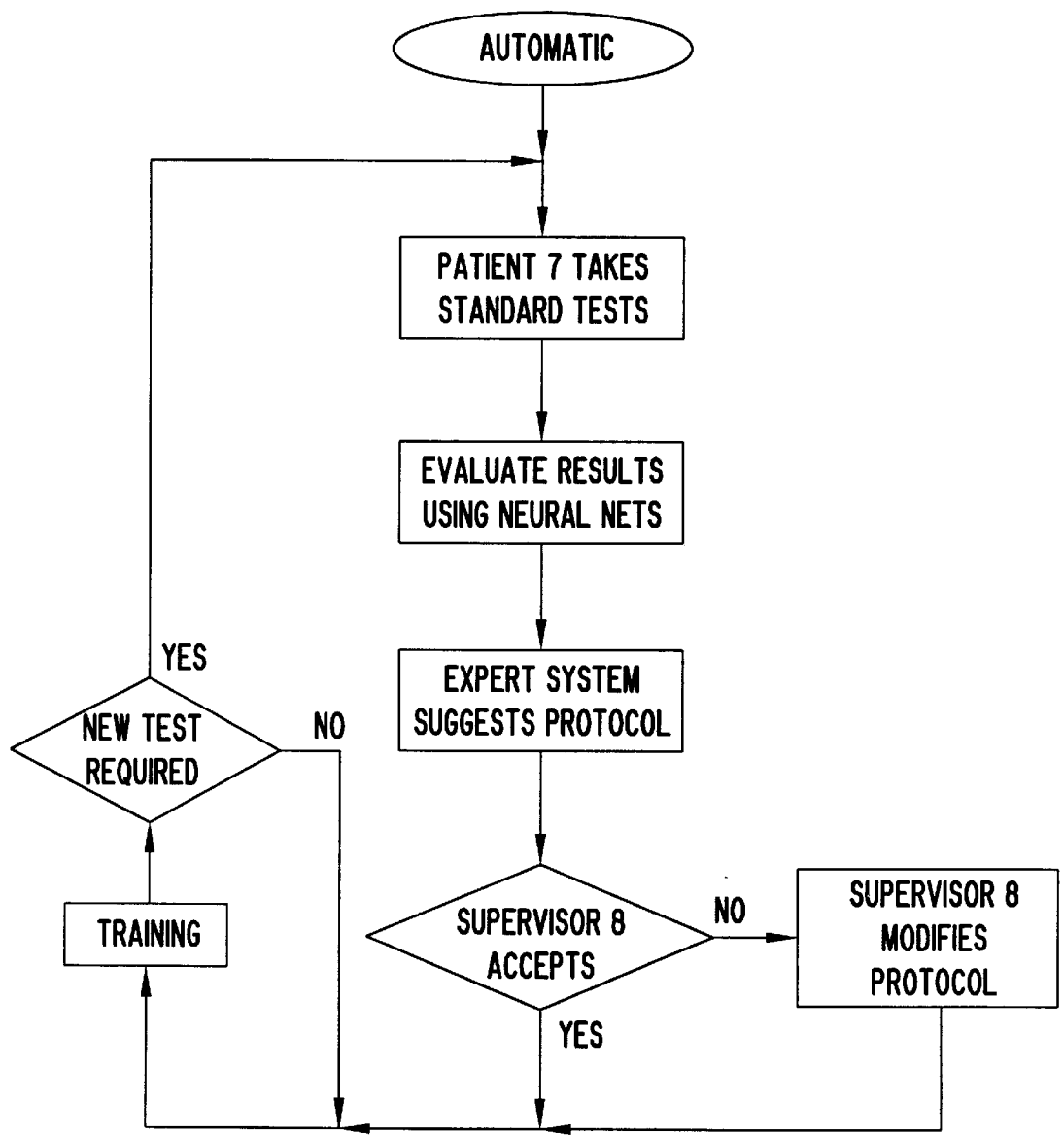
FIG. 12 is a Flow Diagram depicting overall operation of the system in the fully automatic mode.

Overall operation of the system in the (fully) automatic mode is depicted in FIG. 12. Initially, patient 7 is asked to complete a number of standard tests or responses that are appropriate to a physician's assessment of his or her deficit or dysfunction. For example, patient 7 may be asked to complete a flexion/extension response when that individual has previously suffered a stroke. These tests include the acquisition of integrated EMG data as well as positional information obtained from sensors such as goniometers that receive such information from patient 7 via data acquisition circuits 14 of patient station 2. Information from these tests are then evaluated using a neural net that identifies the extent and nature of the deficiency (e.g., spastic response of biceps). The results generated by the neural net are transmitted to an expert system that recommends a rehabilitative protocol including the tasks to be mastered and the elements comprising those tasks. Supervisor 8 may review these recommendations, accept them without change or modify them if necessary. Training may begin once the protocol and tasks have been determined. Training proceeds as described in FIG. 11 within the semi-automatic mode of operation of the entire system. Within the semi-automatic mode, training proceeds until the protocol has been successfully completed. Periodically, patient 7 may repeat the standard tests to reevaluate the extent of the deficit or dysfunction with the possibility of a new or modified protocol recommendation from the expert system.

Figure 13:
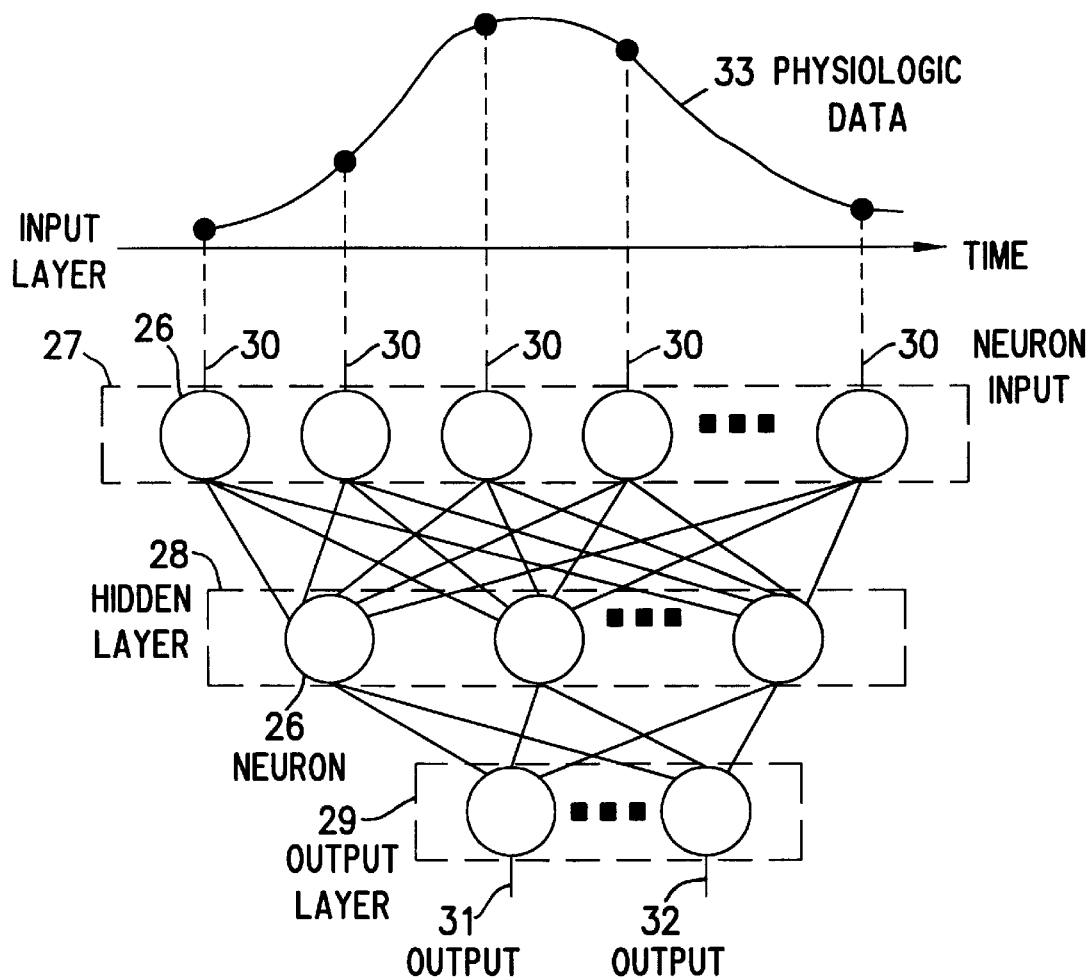
FIG. 13 is a representative functional diagram of a neural net that is organized to recognize and interpret pathological responses from subject 7.

FIG. 13 is a representative functional diagram of a neural net that is organized to recognize and interpret pathological responses from subject 7. (The theory of neural nets is discussed fully in "Fundamentals of Neural Networks by Fausett, Prentice Hall, 1995.) The neural net may consist of a machine (hardware) specifically constructed to carry out the purposes which follow. In the present invention the neural net is simulated as a program on personal computer 15 of either supervisor station 1 or patient station 2.

The net is composed of a multiplicity of prototypical neuron 26 elements interconnected with each other. A single neuron 26 has one or more weighted inputs whose weights can be adjusted by the computer over the course of time. These adjustable weighted inputs are summed together and the results applied to a nonlinear element. The summer and nonlinear element are contained within the circle of neuron 26. In addition to their interconnection, the multiplicity of neuron 26 elements are grouped together into tiers or layers and identified as input layer 27, hidden layer 28, and output layer 29. Input layer 27 accepts sample input 33 which have recorded during the standard test phase of the automatic mode of operation of the system. Inputs 30 of input layer 27 represent, in part, one sample each from the time course of physiologic data 33 from patient 7 where such data has been transformed in patient station 2 and transmitted via communication network 5, local area network 4 and router 3 to supervisor station 1 if necessary. Additional inputs 30 may include patient data such as age, sex, medical history, and other physical characteristics such as weight. If the neural net is presented with data from an abnormal response it will recognize such information but only after it has been "trained" to do so in the following manner:

1. Input samples from the time course of physiological and other data derived from standardized tests carried out by a group of normal subjects as well as a group of disabled subjects are applied to input 30 of the net. In accordance with the values of the weights at the time that each sample is presented, the neural net produces outputs 31 through 32 at each output of output layer 29. Such outputs represent results such as "normal subject," "spastic biceps," "paretic triceps," etc. The group of subjects, both normal and disabled, is referred to as the training set.

2. If the results obtained from outputs 31 through 32 are not in agreement with the conclusions that an expert observer would make, the weights at the inputs of neurons in output layer 29 as well as the weights at the inputs of hidden layer 28 are adjusted according to a rule known to those familiar with the art as Backpropagation. After the weights are adjusted, presentation of the same data at some point in the future would tend to produce the correct results at output layer 29. If the results were initially in agreement with the data, no weight adjustment is required.

3. The procedure described in step 2, above, continues until the neural net correctly identifies practically all training set samples.

4. Test results from a group of new samples is then applied to the neural net without the correction procedure noted in step 2. If the network does not correctly identify practically all of the samples, training is resumed in accordance with step 2 with the addition of this new test group added to the training set.

5. When results from step 4 are satisfactory, the neural net weights are considered to be appropriate and data from subjects (patient 7) that the neural net has not previously encountered can be accepted. Results from outputs 31 through 32 may be supplied to expert system as shown in the Flow Diagram of FIG. 12.

Backpropagation is based on finding the outputs at each layer of the neural net, calculating the errors or differences between the desired outputs and the current outputs, and correcting or adjusting the weights in proportion to the error or discrepancy. This adjustment is made for each layer, and each weighted input for all neurons within that layer, starting with the output layer 29 and proceeding back to the input layer 27.

Figure 14:
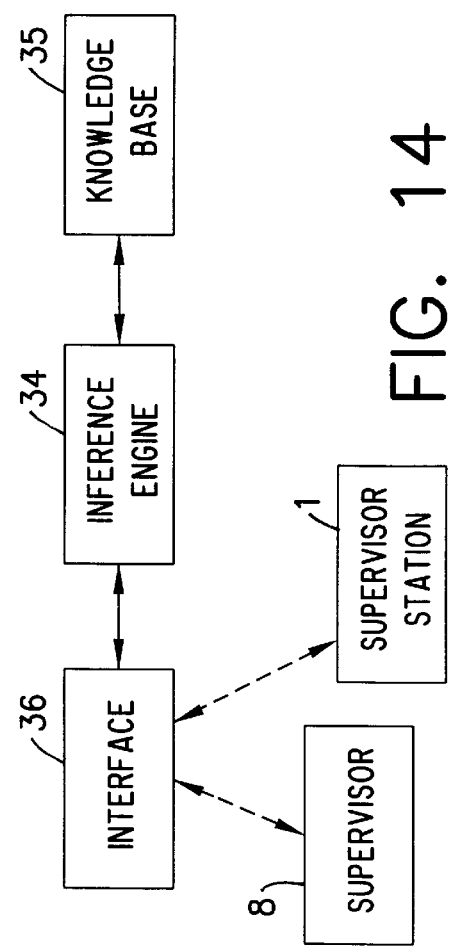
FIG. 14 is a block diagram of an expert system that makes recommendations with respect to the rehabilitative protocol that patient 7 is to pursue.

Results from the neural net are the input conditions or facts that are further interpreted by the expert system which is represented as a block diagram in FIG. 14. When the system is operating in a completely automatic manner as depicted in the Flow Diagram of FIG. 12, the results generated by the neural net in response to inputs from patient 7 undergoing standard tests, are received by the expert system shown in FIG. 14. The entire system is under the control of supervisor 8 who may choose to obtain results from standard test procedures without the benefit of the results of the neural net. The expert system is arranged to draw one or more conclusions when supplied with either facts from the neural net or heuristic information from supervisor 8.

Inference engine 34 and Knowledge base 35 form the heart of the expert system. Interface 36 provides the means by which input data gains access to the Inference engine 34 and Knowledge base 35. (Inference engine 34, Knowledge base 35 and interface 36 are program modules within personal computer 15 of supervisor station 1.) Interface 36 may include graphical aids for input queries (when supplied by a human user) or modifications to Knowledge base 35 (e.g., additions to, deletions from, or alterations of facts or rules within Knowledge base 35). Inference engine 34 translates entries into a form that is compatible with the internal representation of the information within Knowledge base 35. It also translates conclusions into some form of either natural representation (language, speech or vision) or into information that can be used by the training algorithm (depicted in the Flow Diagram shown in FIG. 11). Inference engine 34 includes two kinds of entities: the operations or rules of logical inference; and the control strategy defined as the procedure to be followed for choosing which operation to apply and on which element (fact or predicate phrase) of Knowledge base 35 to apply the operation.

With respect to the representative embodiment of this invention, the expert system includes a number of facts in the form of rules that may include well established logical statements and/or heuristic (practical) information. A sample rule from this invention is represented by the following:

If (biceps contraction is present during elbow extension) then (spastic biceps activity is to be reduced by progressive inhibition is suggested).

(Rules within the expert system module are of the form "If p then q" and may not appear to be grammatically correct. This form is consistent with the representation of knowledge within an expert system data base.). Interface 36 may be supplied either with results from the neural net module or input from supervisor 8. The expert system suggests a conclusion about the assessment of any deficit and proposes a course of rehabilitation. If, for example, the predicate "biceps contraction is present during elbow extension"—as detected by the neural net—is true (a fact), then the expert system will respond with the recommendation "spastic biceps activity is to be reduced by progressive inhibition is suggested." Normally, the Inference engine 34 supports a form of logic known as abductive reasoning which seeks to mimic the decision making processes of humans.

It is noted that certain functionality of the supervisor station 1 and of the patient station 2 of the representative embodiment of the present invention can be implemented utilizing a logic circuit or a computer memory comprising encoded computer-readable instructions, such as a computer program. The functionality of the logic circuit or computer memory has been described in detail above. Generally, the present invention has practical application as it enables medical professionals to monitor a number of patients at the same time and to monitor patients located at remote locations. Moreover in automatic mode, little assistance is needed by the medical professional.

The above described embodiments are merely illustrative of the principles of the present invention. Other embodiments of the present invention will be apparent to those skilled in the art without departing from the spirit and scope of the present invention.

What is claimed is:

1. An interactive intervention system for monitoring a patient suffering from neurological disorders of movement and assisting in patient rehabilitation, comprising:

a patient station for use by a patient in rehabilitative training and including a computer processor;

a supervisor station for use by a medical professional including a computer processor, said patient station and said supervisor station coupled via a concurrent communications network and said supervisor station containing a set of preselected rules for determining a goal for patient rehabilitation;

first sensors for collecting physiologic information from the patient while the patient is undergoing rehabilitative training, the first sensors coupled to the patient station and providing said physiologic information to said patient station as electrical signals, the patient station communicating the physiologic information to the supervisor station in real time;

second sensors for collecting positional information from the patient while the patient is undergoing rehabilitative training, the second sensors coupled to the patient station and providing said positional information to said patient station as electrical signals, the patient station communicating the positional information to the supervisor station in real time;

a patient input device coupled to the patient station enabling the patient to communicate in real time with the medical professional at the supervisor station;

a supervisor output device coupled to the supervisor station enabling the medical professional to receive real time communications from the patient at the patient station;

a supervisor input device coupled to the supervisor station enabling the medical professional to communicate in real time with the patient at the patient station;

a patient output device coupled to the patient station enabling the patient to receive real time communications from the supervisor station; and software means located a the supervisor station, accepting as input the physiologic information and the positional information and determining for the patient a goal to be achieved during rehabilitative training, said goal being determined according to one of the preselected rules and based upon the input physiological information and positional information and said goal communicated to the patient at the patient station while the patient is undergoing rehabilitation.

2. The system of claim 1 wherein the first sensors comprise surface electromyographic electrodes producing electrical signals representative of physiologic processes.

3. The system of claim 1 wherein the second sensors comprise a transducer producing electrical signals representative of physical position.

4. The system of claim 1 wherein the patient input device comprises a microphone.

5. The system of claim 1 wherein the patient input device comprises a keyboard.

6. The system of claim 1 wherein the patient input device comprises a video camera.

7. The system of claim 1 wherein the patient output device comprises a speaker.

8. The system of claim 7 wherein the patient output device outputs sounds representative of the physiologic processes of the patient.

9. The system of claim 7 wherein the patient output device output sounds representative of the physical position of body parts of the patient.

10. The system of claim 1 wherein the patient output device comprises a video monitor.

11. The system of claim 1 wherein the supervisor input device comprises a keyboard.

12. The system of claim 1 wherein the supervisor input device comprises a microphone.

13. The system of claim 1 wherein the supervisor input device comprises a video camera.

14. The system of claim 1 wherein the medical professional reviews the physiologic information and the positional information received at the supervisor station and instructs the patient via the supervisor input device of tasks and movements to be attempted and goals to be achieved during rehabilitative training, the instructions received by the patient at the patient output device.

15. The system of claim 1 wherein the medical professional reviews the communications received from the patient via the patient input device and monitors the physiologic information and the positional information received at the supervisor station and instructs the patient via the supervisor input device of tasks and movements to be attempted and goals to be achieved during rehabilitative training, said instructions received by the patient at the patient output device.

16. The system of claim 1 wherein the patient output device outputs communications received from the supervisor input device, said communications including instructions as to tasks to be attempted and goals to be achieved by the patient.

17. The system of claim 1 wherein the patient output device outputs communications received from the software means.

18. The system of claim 1 wherein the patient output device outputs communications received both from the supervisor input device and the software means.

19. The system of claim 1 further comprising a database of patient information coupled to the supervisor station, the database accessed by the software means when making determinations for a patient.

20. The system of claim 1 further comprising converting means for converting the physiological information and positional information into a visual representation of part of the patient's body.

21. The system of claim 20 wherein the patient output device outputs the visual representation created by the converting means.

22. The system of claim 20 wherein the supervisor output device outputs the visual representation created by the converting means.

23. The system of claim 1 further comprising a plurality of patient stations, each for use by a plurality of patients in rehabilitation.

24. The system of claim 23 wherein each of the plurality of patient stations is used concurrently by each one of the plurality of patients.

25. The system of claim 23 wherein each of the plurality of patient stations is located at a different location.

26. The system of claim 1 wherein the concurrent communications network is the Internet.

27. The system of claim 1 wherein the concurrent communications network includes a satellite.

28. The system of claim 1 wherein the concurrent communications network is one or more local area networks.

29. The system of claim 1 wherein the software means utilizes fuzzy logic reasoning to alter the goal to be achieved during rehabilitative training.

30. The system of claim 1 wherein the software means further comprises:
  a neural network for analyzing patient responses to standard tests to determine a type of neurological disorder, said patient responses being input received at the first sensors and at the second sensors; and
  an expert system, receiving input from the neural network, for determining the goal to be achieved during rehabilitative training.

31. An interactive intervention system for monitoring a subject seeking improved physical performance, comprising:
  a trainee station for use by a subject in physical skill training and including a computer processor;
  a supervisor station for use by a supervisor including a computer processor, said trainee station and said supervisor station coupled via a concurrent communications network said supervisor station containing a set of preselected rules for determining a goal for improved physical performance;
  sensors for collecting information from the subject relating to movements performed by the subject while the patient is undergoing physical skill training, the sensors coupled to the trainee station and providing said information to said trainee station as electrical signals;
  synthesis means for summarizing said information received at the sensors, the trainee station communicating said synthesized information to the supervisor station in real time;
  a trainee input device coupled to the trainee station enabling the subject to communicate in real time with the supervisor at the supervisor station;
  a supervisor output device coupled to the supervisor station to output to the supervisor said synthesized information and communications received from the subject at the trainee station;
  a supervisor input device coupled to the supervisor station enabling the supervisor to communicate in real time with the subject at the trainee station;
  a trainee output device coupled to the trainee station to output to the subject said synthesized information and communications received from the supervisor station; and
  software means accepting as input the information received at the sensors and determining for the subject a goal to be achieved during training, said goal being determined according to one of the preselected rules and based upon the input physiological information and positional information and said goal communicated to the subject at the trainee output device while the trainee is undergoing skill training.

32. The system of claim 31 wherein the sensors comprise surface electromyographic electrodes producing electrical signals representative of physiologic processes.

33. The system of claim 31 wherein the sensors comprise a transducer producing electrical signals representative of physical position.

34. The system of claim 31 wherein the software means is located at the trainee station.

35. The system of claim 31 wherein the software means is located at the supervisor station.

36. The system of claim 31 wherein the trainee station is located remotely with respect to the supervisor station.

37. The system of claim 31 wherein the trainee station is located locally with respect to the supervisor station.

38. The system of claim 31 wherein the supervisor reviews the synthesized information received at the supervisor station and instructs the subject via the supervisor input device of tasks to be attempted and goals to be achieved by the subject during training, the instructions received by the subject at the trainee output device.

39. The system of claim 31 wherein the supervisor reviews the communications received from the subject via the trainee input device and the synthesized information received at the supervisor station and instructs the subject via the supervisor input device of movements to be attempted during training, said instructions received by the subject at the trainee output device.

40. The system of claim 31 further comprising a database of subject information coupled to the supervisor station, the database accessed by the software means when making determinations for a subject.

41. The system of claim 31 further comprising a plurality of trainee stations, each for use by a plurality of subjects in skill training.

42. The system of claim 41 wherein each of the plurality of trainee stations is used concurrently, the supervisor station concurrently monitoring training at each trainee station.

43. The system of claim 41 wherein each of the plurality of trainee stations is located at a different site.

44. The system of claim 31 wherein the software means utilizes fuzzy logic reasoning to alter the goal to be achieved during training.

45. The system of claim 44 wherein the software means further comprises:
a neural network for analyzing subject responses to standard tests to determine a type of skill deficiency, said subject responses received at the sensors; and
an expert system, receiving input from the neural network, for determining the goal to be achieved during training.

46. The system of claim 31 wherein the subject is a patient suffering from a neurological disorder of movement and the physical skill training is rehabilitative training.

47. The system of claim 31 wherein the subject is a music student and the physical skill training comprises learning a musical instrument.

48. The system of claim 31 wherein the subject is a sportsman and the physical skill training comprises improvement in movement during sports.

49. An interactive intervention system for monitoring a patient suffering from neurological disorders of movement and assisting in patient rehabilitation, comprising:
a patient station for use by a patient in rehabilitative training and including a computer processor;
a supervisor station for use by a medical professional including a computer processor, said patient station and said supervisor station coupled in a concurrent communications network;
sensors for collecting movement information from the patient relating to movements performed by the patient while the patient is undergoing rehabilitative training, the sensors coupled the patient station and providing the movement information to said patient station as electrical signals;
a supervisor output device coupled to the supervisor station to output the movement information to the medical professional;
a patient output device coupled to the patient station to output the movement information in graphical form to the patient;
a neural network for analyzing patient responses to standard tests performed in rehabilitative training to determine a type of neurological disorder, said patient responses received at the sensors; and
an expert system, receiving input from the neural network and the sensors, for determining a training task and a set of subgoals for that task to be achieved during rehabilitative training, said training task and a first one of the subgoals output to the patient at the patient output device while the patient is undergoing rehabilitation and said subgoal being modified based upon collected movement performed by the patent.

50. The system of claim 49 wherein the sensors comprise surface electromyographic electrodes producing electrical signals representative of physiologic processes.

51. The system of claim 50 wherein the sensors further comprise a transducer producing electrical signals representative of physical position.

52. The system of claim 49 wherein the goal to be achieved is output at the supervisor output device.

53. The system of claim 49 further comprising a supervisor input device coupled to the supervisor station enabling the medical professional to communicate in real time with the patient at the patient station.

54. The system of claim 53 wherein the medical professional reviews the movement information received at the supervisor station and instructs the patient via the supervisor input device of tasks to be attempted and goals to be achieved by the patient during rehabilitative training, the instructions received by the patient at the patient output device.

55. The system of claim 53 wherein the medical professional reviews the communications received from the patient via the patient input device and the movement information received at the supervisor station and instructs the patient via the supervisor input device of movements to be attempted during rehabilitative training, said instructions received by the patient at the patient output device.

56. The system of claim 49 further comprising a database of patient information coupled to the supervisor station.

57. The system of claim 49 further comprising a plurality of patient stations, each for use by a plurality of patients in rehabilitation.

58. The system of claim 57 wherein each of the plurality of patient stations is used concurrently.

59. The system of claim 58 wherein each of the plurality of patient stations is located at a different site.

60. The system of claim 49 wherein the goal determined by the expert system is communicated to the patient at the patient station without need for human intervention.

61. The system of claim 49 wherein the sensors further comprise:
means for measuring electrical activity generated in muscles;
means for measuring spatial displacements of limb segments; and
means for measuring forces generated for acquisition of objects and for mobility.

62. The system of claim 49 wherein the patient comprises a subject with skill deficiency and wherein the rehabilitation training comprises training to obtain improved physical performance and wherein the medical professional comprises a trainer and wherein the neurological disorder comprises a skill deficiency.

63. An interactive intervention system for concurrently monitoring of a plurality of patients at remote locations, comprising:

a plurality of patient stations, each patient station for use by one of the plurality of patients and including a computer processor;

a plurality of first sensors for collecting physiologic information from a patient, each one of the first sensors coupled to one of the patient stations and providing said physiologic information to said patient station as electrical signals;

a plurality of second sensors for collecting physical information from the patient, each one of the second sensors coupled to one of the patient stations and providing said positional information to said patient station as electrical signals;

a plurality of patient input devices, each coupled to one of the patient stations, for allowing said patient to send real time messages via the patient station;

a plurality of patient output devices, each coupled to one of the patient stations, for allowing said patient to receive real time messages at the patient station; and a supervisor station, coupled in a concurrent communications network and located remotely with respect to each one of the plurality of patient stations, the supervisor station including a computer processor, a set of preselected rules for determining a goal for patient rehabilitation, a supervisor input device to send real time messages to said patient stations, a supervisor output device for receiving real time messages from said patient stations, and software means accepting said physiologic information and said positional information from said patient stations and determining for each patient a goal to be achieved, said goal being determined according to one of the preselected rules and based upon the input physiological information and positional information and said goal communicated to the appropriate patient by the supervisor station without human intervention in real time while the patient is undergoing rehabilitation.

64. The system of claim 63 wherein the supervisor output device concurrently outputs information relating to the plurality of patients.

65. The system of claim 63 further comprising means for allowing a medical professional to select one of a plurality of modes for each patient, the plurality of modes including a manual mode controlled by the medical professional, a semiautomatic mode, and an automatic mode controlled by the software means.

66. The system of claim 65 further comprising means for allowing the medical professional to intervene when the system is in semiautomatic and automatic modes.

67. In a concurrent communications network, a computer-based method for monitoring a patient suffering from neurological disorders of movement and assisting in patient rehabilitation comprising the steps of:

at a supervisor station, determining a task for the patient, the task having a goal and storing a set of preselected rules to modify that goal;

receiving the task from the supervisor station;

instructing a patient to perform the task;

collecting physiologic information from the patient as the patient performs that task;

electronically communicating the physiologic information to the supervisor station;

collecting positional information from the patient as the patient performs the task;

communicating the positional information to the supervisor station;

at the supervisor station, outputting the physiologic information and the positional information to a medical professional;

automatically modifying the goal to be achieved, said goal modified according to one of the preselected rules and based upon the collected positional information and the collected physiologic information; and communicating the modified goal to the patient while the patient is undergoing rehabilitation.

68. The method of claim 67 wherein the step of automatically modifying further comprises the step of utilizing a set of fuzzy logic algorithms that alter response goals based upon past experience.

69. The method of claim 67 wherein the step of automatically modifying takes place at the supervisor station.

70. In a concurrent communications network, a computer-based method for monitoring a trainee with a skill deficiency and assisting in movement training, comprising the steps of:

at a computer station, obtaining information about the trainee from a database;

receiving a test from the computer station;

instructing a trainee to perform the test;

collecting physiologic information from the trainee as the trainee performs the test;

electronically communicating the physiologic information to the computer station;

collecting positional information from the trainee as the trainee performs the test;

communicating the positional information to the computer station;

at the computer station, evaluating the physiologic information and the positional information received to identify the extent of the trainee's skill deficiency;

at the computer station, determining a trainee improvement protocol comprising tasks with each task comprising a set of subgoals; and electronically communicating the tasks and a first one of the subgoals to the trainee.

71. The method of claim 70 further comprising the steps of:

receiving the tasks from the central station;

instructing the trainee to perform the tasks;

collecting physiologic information from the trainee as the trainee performs the tasks;

electronically communicating the physiologic information to the central station;

collecting positional information from the trainee as the trainee performs the tasks;

communicating the positional information to the central station;

at the central station, outputting the physiologic information and the positional information to the professional;

automatically modifying the task based upon the collected positional information and the collected physiologic information; and communicating the modified task to the trainee.

72. The method of claim 71 wherein the step of automatically modifying further comprises the step of utilizing a set of fuzzy logic algorithms that alter response goals based upon past experience.

73. The method of claim 70 wherein the step of evaluating further comprises the step of utilizing a neural network to analyze the physiologic information and the positional information.

74. The method of claim 73 wherein the step of determining a trainee improvement protocol further comprises the step of utilizing an expert system to determine a goal to be achieved during training.

75. The method of claim 70 wherein the trainee is a patient and wherein the skill deficiency is a neurological disorder.

76. The method of claim 71 wherein the trainee is a music student and wherein the skill deficiency is learning an instrument.

77. The method of claim 70 further comprising the steps of:

collecting force information from the trainee as the trainee performs the test; and communicating the force information to the central station.

78. The method of claim 71 further comprising the steps of:

collecting force information from the trainee as the trainee performs the tasks; and electronically communicating the force information to the central station.

* * * * *